(12) United States Patent
Loewy et al.

(10) Patent No.: US 6,287,595 B1
(45) Date of Patent: Sep. 11, 2001

(54) BIOMEDICAL ASSAY DEVICE

(75) Inventors: Zvi Loewy, Fairlawn; Dennis Lee Matthies, Princeton, both of NJ (US)

(73) Assignee: Delsys Pharmaceuticals Corporation, Monmouth Junction, NJ (US)

( * ) Notice: Subject to any disclaimer, the term of this patent is extended or adjusted under 35 U.S.C. 154(b) by 0 days.

(21) Appl. No.: 09/535,522

(22) Filed: Mar. 24, 2000

Related U.S. Application Data

(63) Continuation-in-part of application No. 09/095,616, filed on Jun. 10, 1998.

(51) Int. Cl.[7] ............... A61K 9/52; A61K 9/48; A61K 9/20; A61K 9/22
(52) U.S. Cl. ............ 424/457; 424/451; 424/464; 424/468
(58) Field of Search .................. 424/451, 457, 424/464, 468

(56) References Cited

U.S. PATENT DOCUMENTS

| | | | |
|---|---|---|---|
| 4,029,757 | 6/1977 | Mlodezeniec et al. | 424/452 |
| 4,029,758 | 6/1977 | Mlodezeniec et al. | 424/27 |
| 4,069,084 | 1/1978 | Mlodezeniec et al. | 156/378 |
| 4,072,551 | 2/1978 | Dabal et al. | 156/378 |
| 4,126,502 | 11/1978 | Dabal et al. | 156/184 |
| 4,126,503 | 11/1978 | Gardner | 156/184 |
| 4,128,444 | 12/1978 | Mlodozenic | 156/64 |
| 4,128,445 | 12/1978 | Sturzenegger et al. | 156/64 |
| 4,154,636 | 5/1979 | Motoyama et al. | 156/243 |
| 4,197,289 | 4/1980 | Sturzenegger et al. | 424/21 |
| 4,307,555 | 12/1981 | Mlodozeniec et al. | 53/53 |
| 5,207,217 | 5/1993 | Cocozza et al. | 128/203.21 |
| 5,699,649 | 12/1997 | Abrams et al. | 57/245 |

FOREIGN PATENT DOCUMENTS

| | | |
|---|---|---|
| 0065370 A | 11/1982 | (EP) . |
| WO98 20 861 A | 5/1998 | (WO) . |

*Primary Examiner*—Shelley A. Dodson
(74) *Attorney, Agent, or Firm*—Carella Byrne Bain GilfillanCecchi; Elliot M. Olstein; William Squire

(57) ABSTRACT

The present invention provides an integrated structural unit that includes a diagnostic form that includes at least one active ingredient that is present in an amount that advantageously does not vary by more than about five percent from a predetermined target amount. In one embodiment, the unit form comprises a substrate, a deposit that is disposed on the substrate, and a spreading layer that overlies the deposit and is used to retain and spread a sample of liquid which is to be assayed. The deposit comprises a powder, including the active ingredient(s). The diagnostic form is created via a dry powder deposition apparatus that electrostatically deposits the powder on the substrate utilizing an electrostatic chuck and charged powder delivery apparatus.

11 Claims, 12 Drawing Sheets

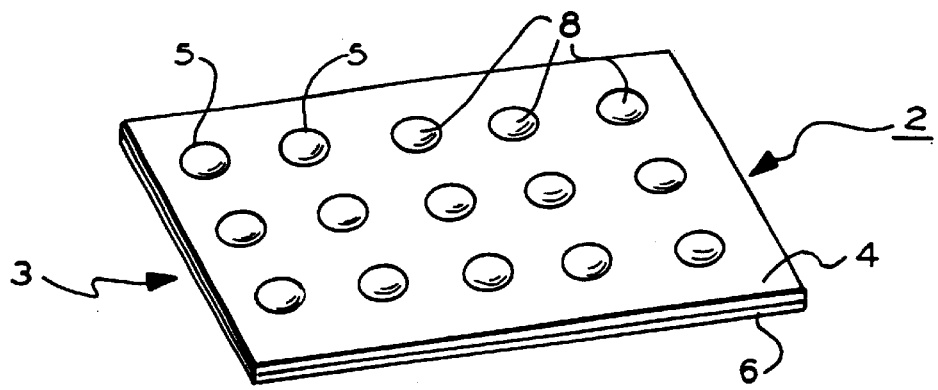
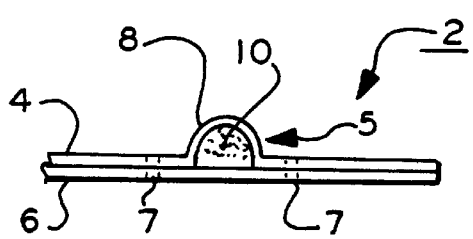
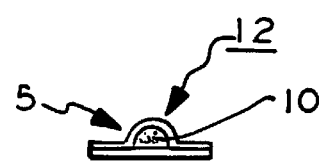
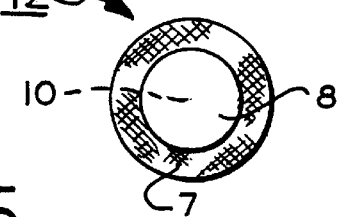
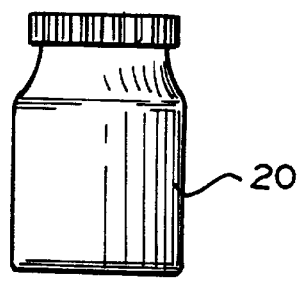

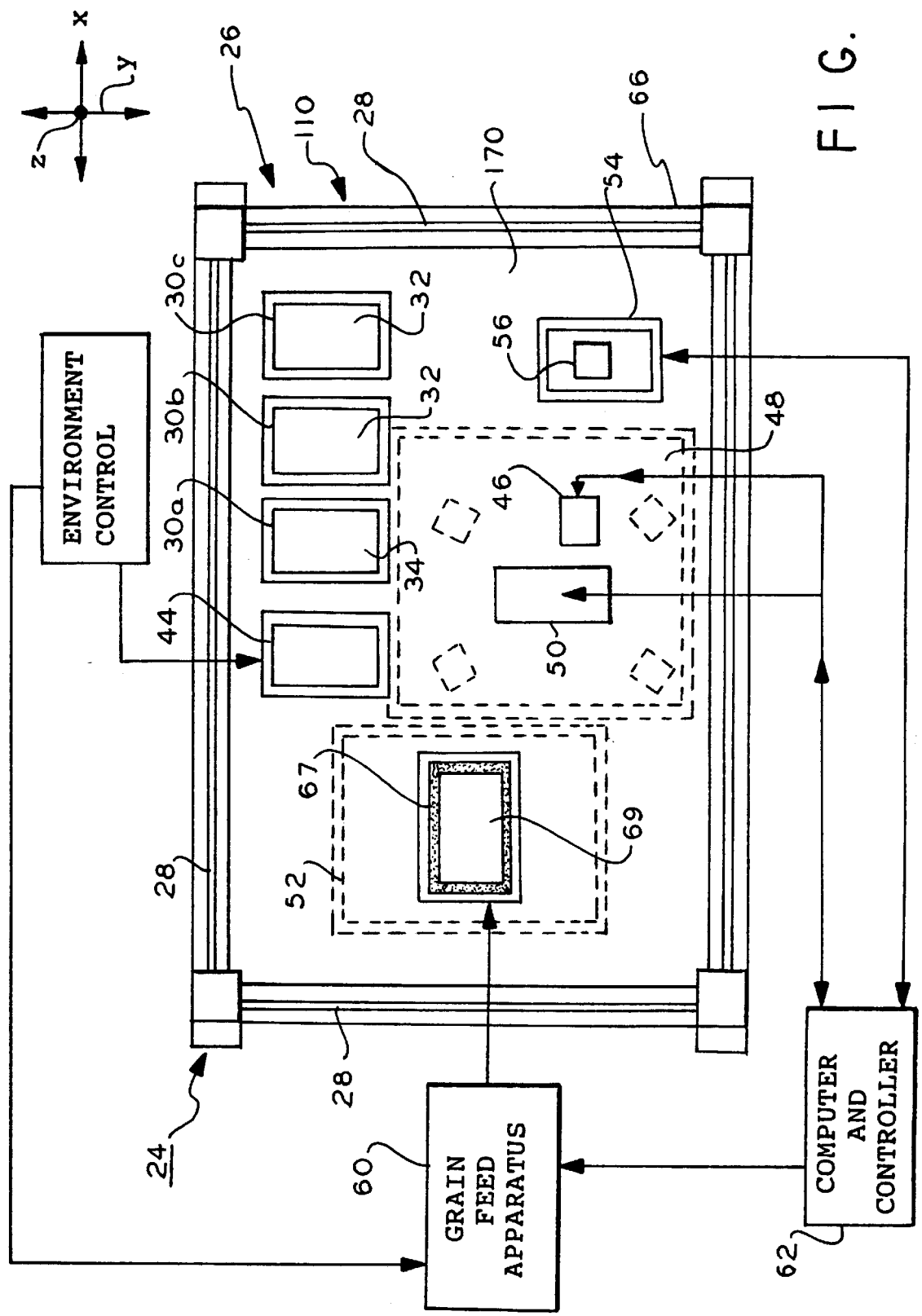

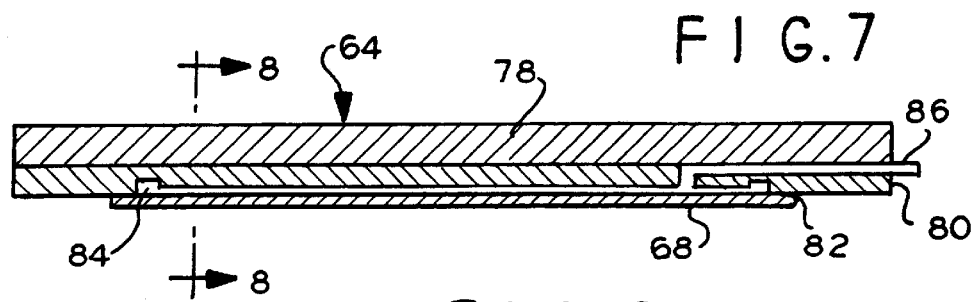
FIG. 7
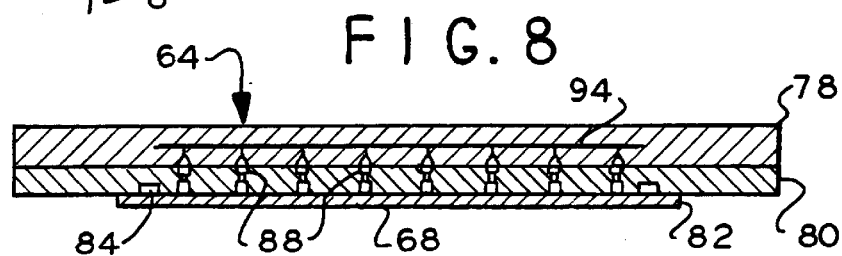
FIG. 8
FIG. 9
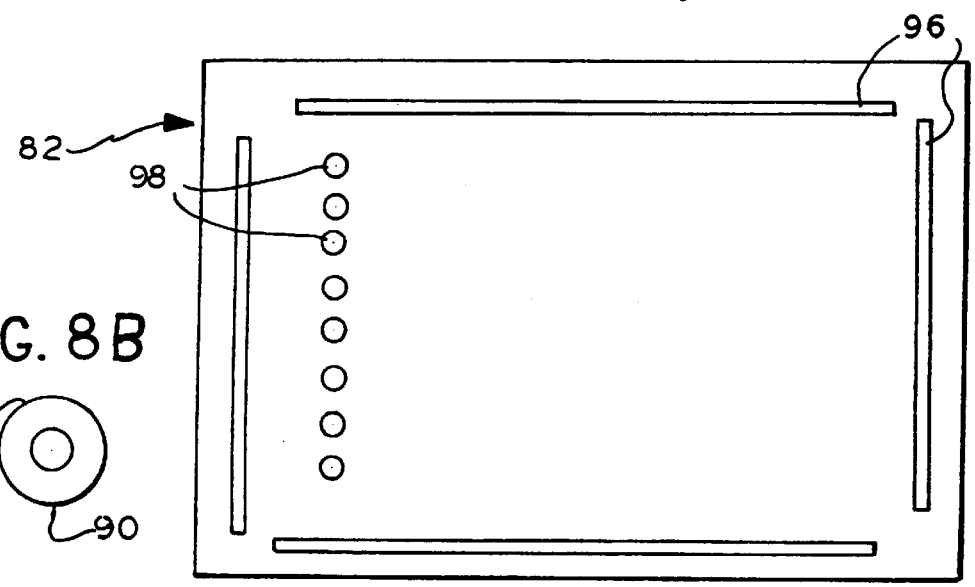
FIG. 8B
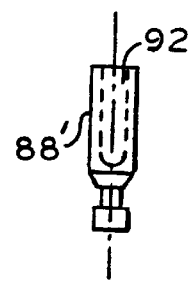
FIG. 8A
FIG. 10
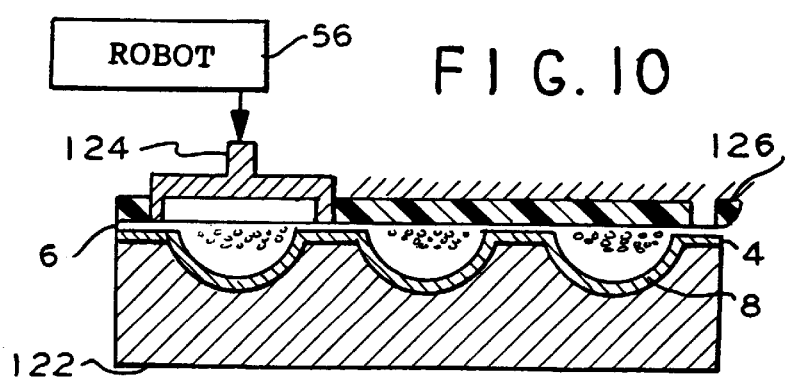

BIOMEDICAL ASSAY DEVICE

This application is a continuation-in-part of application Ser. No. 09/095,616 filed Jun. 10, 1998.

CROSS REFERENCE TO RELATED CASES

The following U.S. patents are of interest: U.S. Pat. No. 5,669,973 issued Sep. 23, 1997 to Pletcher et al., APPARATUS FOR ELECTROSTATICALLY DEPOSITING AND RETAINING MATERIALS UPON A SUBSTRATE; U.S. Pat. No. 5,714,007 issued Feb. 03, 1998 to Pletcher et al., APPARATUS FOR ELECTROSTATICALLY DEPOSITING A MEDICAMENT POWDER UPON PREDEFINED REGIONS OF A SUBSTRATE; U.S. Pat. No. 5,788,814 issued Aug. 04,1998 to Sun, CHUCKS AND METHODS FOR POSITIONING MULTIPLE OBJECTS ONA SUBSTRATE; U.S. Pat. No. 5,753,302 issued May 19, 1998 to Sun et al., ACOUSTIC DISPENSER; U.S. Pat. No. 5,846,595 issued Dec. 08, 1998 to Sun et al., ELECTROSTATIC CHUCKS; U.S. Pat. No. 5,858,814 issued Jan. 12, 1999 to Sun et al., ELECTROSTATIC CHUCKS; U.S. Pat. No. 5,871,010 issued Feb. 16, 1999 to Datta et al., INHALER APPARATUS WITH MODIFIED SURFACES FOR ENHANCED RELEASE OF DRY POWDERS; U.S. Pat. No. 6,007,630 issued Dec. 28, 1999 to Pletcher et al., METHOD AND APPARATUS FOR ELECTROSTATICALLY DEPOSITING A MEDICAMENT POWDER UPON PREDEFINED REGIONS OF A SUBSTRATE; U.S. Pat. No. 6,074,688 issued Jun. 13, 2000 to Pletcher et al., METHOD AND APPARATUS FOR ELECTROSTATICALLY DEPOSITING A MEDICAMENT POWDER UPON PREDEFINED REGIONS OF A SUBSTRATE; U.S. Pat. No. 6,004,752 issued Dec. 21, 1999 to Loewy et al., DEPOSITED REAGENTS FOR CHEMICAL PROCESSES; U.S. Pat. No. 6,045,753 issued Apr. 04, 2000 to Loewy et al., SOLID SUPPORT WITH ATTACHED MOLECULES; U.S. Pat. No. 6,096,368 issued Aug. 01, 2000 to Sun, BEAD TRANSPORTER CHUCKS USING REPULSIVE FIELD GUIDANCE; U.S. Pat. No. 5,988,432 issued Nov. 23, 1999 to Sun, BEAD MANIPULATING CHUCKS WITH BEAD SIZE SELECTOR; U.S. Pat. No. 6,168,666 issued Jan. 01, 2001 to Sun, FOCUSED ACOUSTIC BEAD CHARGER/DISPENSER FOR BEAD MANIPULATING CHUCKS; U.S. Pat. No. 6,149,774 issued Nov. 21, 2000 to Sun et al., AC WAVEFORMS BIASING FOR BEAD MANIPULATING CHUCKS; and U.S. Pat. No. 6,063,194 issued May 16 2000 to Desai et al., DRY POWDER DEPOSITION APPARATUS.

The following U.S. patent applications are of interest: Ser. No. 09/095,321 filed Jun. 10, 1998 by Sun et al., APPARATUS FOR CLAMPING A PLANAR SUBSTRATE and Ser. No. 09/095,616 filed Jun. 10, 1998 by Chrai et al., PHARMACEUTICAL PRODUCT.

FIELD OF THE INVENTION

The present invention relates generally to unit dosage or unit diagnostic forms and an apparatus and method for making such unit forms.

BACKGROUND OF THE INVENTION

In the pharmaceutical industry, pharmaceutical products including diagnostic products comprise a container (e.g., a bottle, a blister pack or other packaging) containing a plurality of "unit dosage forms" or "unit diagnostic forms." Each of such unit forms contains a pharmaceutically- or biologically-active ingredient or ingredients and inert or inactive ingredient(s).

The pharmaceutically-active ingredient typically forms a drug. The diagnostic form may comprise a reagent or the like for use in diagnostic tests, and may be part of a set which includes several different reagents or active ingredients. Moreover, the diagnostic form may comprise an antibody, an antigen, or labeled forms thereof and the like.

A pharmaceutically- or biologically-active ingredient for use in a unit form may be supplied as a powder comprising a plurality of active-ingredient particles. Such active-ingredient particles are combined with inert or inactive ingredient particles to form a plurality of "major particles." The major particles are quite small, with dimensions on the order of microns. Such major particles are typically combined with one another to create the final unit dosage or diagnostic form (e.g., tablet, caplet, test strip, capsule, etc.).

There may be significant variation in the amount of pharmaceutically- or biologically-active ingredient in one major particle and the next. Since a large number of major particles are required to create a final unit form, the aforedescribed particle-to-particle variation may result in a substantial variation in the amount of active ingredient between one unit form and the next. Thus, any given final form may contain substantially more or less than a desired amount of active ingredients.

Destructive analytical screening procedures are conventionally performed to assess the amount of active ingredient (s) in final unit forms. Since such procedures destroy the unit forms, a statistical sampling is performed whereby a relatively small number of forms per batch are actually sampled and tested. Such screening procedures disadvantageously provide no assurance that all forms in a given batch contain a desired amount of the pharmaceutically- or biologically-active ingredients. In fact, such statistical methods practically "guarantee" that a statistically determinable percentage of the forms in each batch will be out of specification.

As such, the art would benefit from a method and apparatus that provides improved control over the active-ingredient content of unit dosage and diagnostic forms.

SUMMARY OF THE INVENTION

In one embodiment, the present invention provides a product comprising a plurality of pharmaceutical unit dosage forms or unit diagnostic forms (collectively, "unit forms"). Each form includes at least one active ingredient that is present in an amount that advantageously does not vary by more than about five percent from a predetermined target amount.

In one embodiment, the unit form comprises a substrate, an active ingredient deposited thereon, and a cover layer that covers the active ingredient and is joined (e.g., via welding, adhesives, etc.) to the substrate in the proximity of the active ingredient.

In the illustrated embodiments, the product is made via a dry deposition apparatus that deposits powder/grains on the substrate. In one embodiment, the apparatus comprises an electrostatic chuck, a charged powder delivery apparatus, and an optical detection system. The substrate is engaged to the electrostatic chuck for the dry deposition of powder. The chuck has at least one collection zone at which a powder-attracting electrical field is developed. The charged powder-delivery apparatus directs charged powder for electrostatic deposition to the substrate at the collection zone(s). The optical detection system quantifies the amount of powder deposited.

In some embodiments, the dry deposition apparatus also includes an electronic processor for controlling depositions responsive to sensor inputs. Such sensor inputs advantageously include one or more deposition sensors that are disposed on or adjacent to the electrostatic chuck and that provide data pertaining to the amount of powder deposited. Responsive to sensor data, the electronic processor adjusts deposition parameters, as necessary. Controllable parameters include powder flux through the powder-delivery apparatus and applied voltage at the collection zone(s).

In still other embodiments, the present dry deposition apparatus advantageously includes a variety of other elements that are described in detail later in this Specification.

BRIEF DESCRIPTION OF THE DRAWINGS

FIG. 1 is an isometric view of a strip package of pharmaceutical unit dosage or diagnostic forms;

FIG. 1a is a plan schematic view of a system for making a product according to one embodiment of the present invention;

FIG. 2 is a sectional elevation view of a portion of the package of FIG. 1 showing one of the forms;

FIG. 3a is a sectional elevation view of a separated unit form of the embodiment of FIGS. 1 and 2;

FIG. 3b is a side elevation view of a tablet form of the present invention in a second embodiment;

FIG. 4 is a plan view of the embodiment of FIG. 3a;

FIG. 5 is a side elevation of a container package for the unit forms of FIGS. 3a and 3b;

FIG. 6 is a fragmented isometric view of a package for the strip unit forms of the embodiment of FIG. 1;

FIG. 7 is a schematic side elevation sectional view of a robotically operated electrostatic chuck for carrying a substrate forming the unit forms of an embodiment of the present invention;

FIG. 8 is a side elevation sectional view of the chuck of FIG. 7 taken along lines 7—7;

FIG. 9 is a plan view of a gasket employed in the embodiment of FIGS. 7 and 8;

FIG. 10 is a side elevation sectional schematic view of the formation of a package of the present invention at a lamination station;

FIG. 19 is schematic plan view of a detection array at the measurement station of the embodiment of FIG. 1a;

DETAILED DESCRIPTION

Figure 11:
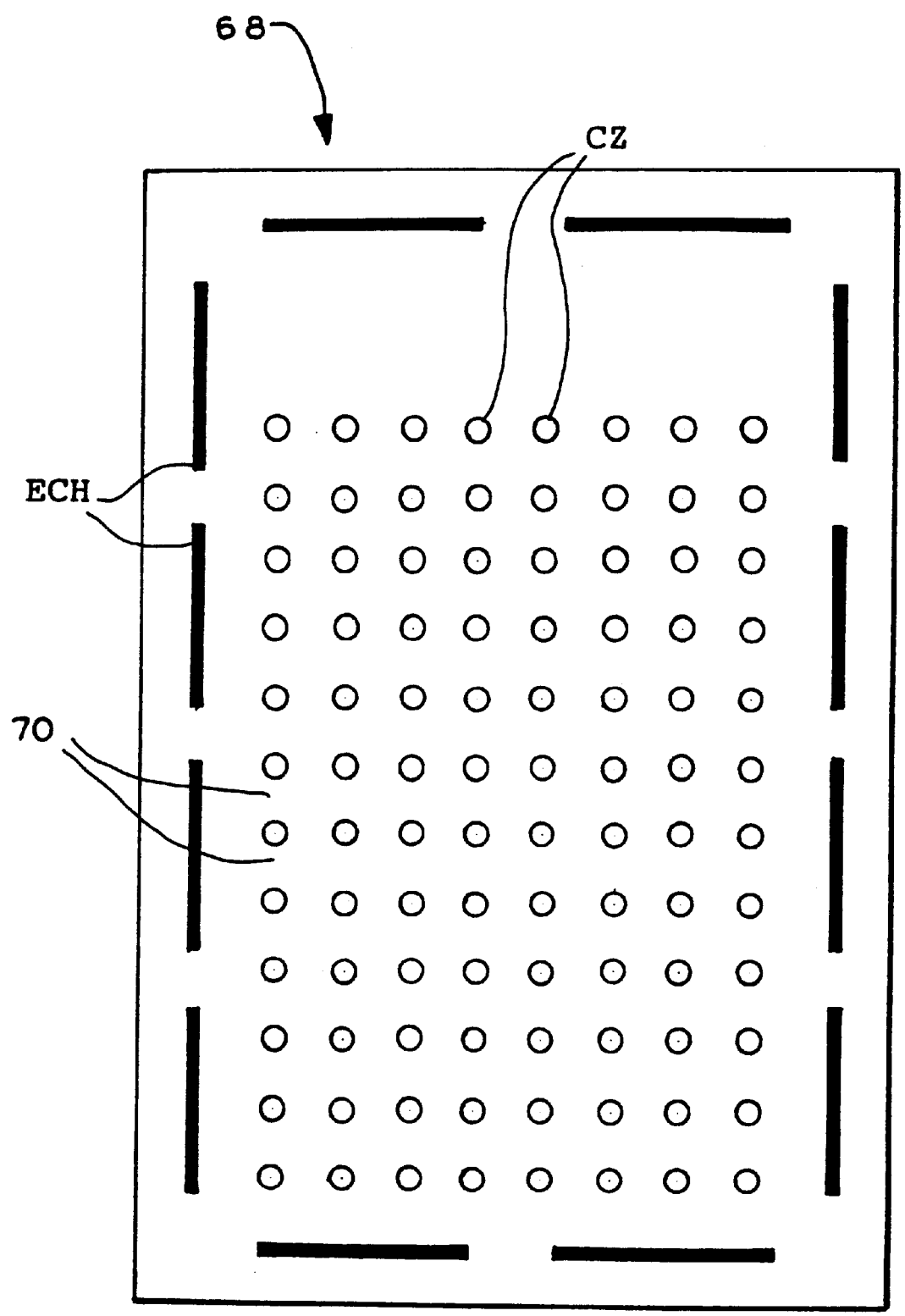
FIG. 11 is a plan view of a front surface the electrostatic chuck of FIG. 7 without the gasket in place showing the surface of the chuck showing through holes and collection zones for active powder/grains.

In FIGS. 1 and 2, package 2 comprises a strip 3 of an array of product forms 5. The strip 3 is formed from larger strips as explained in more detail below. The package 2 further comprises a cover substrate 4 and a base substrate 6. The cover substrate 4 is a planar flexible film sheet as described below and includes an array of semi-spherical bubbles or depressions 8 arranged in columns and rows. The package 2 may comprise an array of three by five unit pharmaceutical or diagnostic dosage forms by way of example. More or fewer may be provided as desired. The base substrate 6 is a planar film sheet. The dry powder active ingredient 10 in the form of powder/grains is deposited between the substrates 4 and 6 in each depression 8 as will be described below. The unit product forms 5 are created by heat or ultrasonic annular welds 7 formed about the depressions 8. The welds may also be formed by a suitable adhesive or the like.

In the description that follows, the term unit pharmaceutical or diagnostic dosage form includes a separate discrete active ingredient or ingredients whether or not on a discrete separate substrate, whether or not the substrate is edible, that may be used as a dosage for pharmaceutical purposes or as an element(s) for diagnostic purposes, whether or not encapsulated, capable of being packaged or otherwise available for end use as a unit.

The term dry deposited refers to a material deposited without a liquid vehicle.

Grains are, for the purposes of this application, either aggregates of molecules or particles, typically of at least about 3 nm average diameter, preferably at least about 500 nm or 800 nm average diameter, and are preferably from about 100 nm to about 5 mm diameter, for example, about 100 nm to about 500 nm. Grains are, for example, particles of a powder, or polymer structure that can be referred to as "beads." Beads can be coated, have adsorbed molecules, have entrapped molecules, or otherwise carry other substances.

The active ingredient 10 may be a pharmaceutical product, i.e., a drug, or a diagnostic product useful for biological diagnostic laboratory or medical related purposes, for example.

In FIGS. 3a and 4, a second embodiment of the product form may comprise discrete capsules 12. The capsules 12 are created by severing the individual product forms from the strip forming the package 2.

In FIG. 3b, the product form may comprise a tablet 14. The tablet 14 comprises an active ingredient 16 deposited in powder/grain form on an edible inert substrate 18. Reference is made to the aforementioned patents for more detail regarding the formation of such tablets.

In FIG. 5, a bottle 20 forms a container for the capsules 12 or tablets 14. In FIG. 6, a box or similar packaging device houses the strips 3.

The substrates 4 and 6 are preferably films typically flexible planar thermoplastic material having a thickness for example of about 0.001 inches (0.0254 mm). Suitable plastic substrate materials include polyvinylacetate, hydroxypropylmethylcellulose and polyethylene oxide films.

In FIG. 1a, system 24 for fabricating the unit pharmaceutical or diagnostic dosage forms 5 comprises a robotic platform 26 in which the product forms 5 are created in which dry powder/grains are deposited on the substrates. The platform 26 is in an environmental enclosure comprising thermoplastic, e.g., acrylic, sheet walls 28 and including a ceiling (not shown).

The platform 26 comprises substrate input/output stations 30a, 30b and 30c at which framed substrate assemblies 32 and 34 are stored for later use or processing. The platform 26 includes alignment station 44, measurement station 48 employing dose measurement apparatus 50, deposition station 52, and lamination station 54.

The framed substrate assembly 32 at stations 30b and 30c comprises a rectangular cover substrate 36 having an eight by twelve array of depressions 8, for example. Assembly 32 includes a metal frame (not shown), e.g., sheet aluminum, to which the substrate is secured. The frame includes guide holes (not shown). The guide holes mate with guide pins (not shown) at the input/output stations 30b and 30c, FIG. 1a, the robot head (not shown) of robot 56 at lamination station 54. The substrates 36 form the cover 4, FIG. 1.

The substrates 34 at station 30a each form the base 6, FIG. 1. The substrate of assembly 34 differs from the substrate 36 in that no depressions are formed in the substrate of assembly 34. The substrate of assembly 34 is also attached to a frame such as frame 38. The frames via their guide holes mate in guide pins (not shown) at the input/output station 30a and the alignment station 44 which aligns the frames 38 to the robot head of robot 46 at the measurement station 48.

Alignment station 44 aligns the substrate assembly 34 to its mating pick up robot 46 located at measurement station 48 for providing accurate processing of the deposition powder/grains on the substrate of assembly 34. Measurement station 48 includes a dose measurement apparatus 50 having a measurement window (e.g., glass-not shown). The platform 26 includes a powder/grain deposition station 52 and a lamination station 54 at which is located a second robot 56. The robot 46 picks up and transports the base 6 substrate assemblies 34 and the robot 56 picks up and transports the cover 4 substrate assemblies 32 from the corresponding input/output stations.

Charged powder/grains are delivered to the robotic platform deposition station 52 from powder/grain feed apparatus 60, which also is in an environmentally controlled enclosure. Environment control 62 controls the environment of the platform 25 and apparatus 60 by controlling temperature, pressure and humidity. Computer and controller 62 operates the powder/grain feed apparatus, the robots of the platform 26 and the measurements made at station 48 by apparatus 50.

The deposition station 52 includes a deposition gasket 67 surrounding a deposition chamber 69 having an opening through which charged powder/grains are forced to flow during deposition onto the overlying substrate of assembly 34.

The robots of platform 26 can be based, for example, on a Yaskawa RobotWorld linear Motor Robot. The robots are linked to rails (not shown) for providing x-y movement via x-y linear stepper motors (not shown). Each robot has telescoping components under servo control (not shown) for moving a substrate receiver attached its head (not shown) in the z axis normal to the x-y plane. Robot 46 has a receiver head 64, FIGS. 7, 8, 13 and 14 to which an electrostatic chuck 68, FIGS. 7 and 8, is attached. Robot 56 has an ultrasonic weld unit attached to its head for laminating the cover 4 and base 6 substrates at the lamination station 54.

Also, the robots 46 and 56 have control components to provide servo control to rotate the respective robotic head and receiver, such as receiver 64 in the x-y plane. Compressed air or other gases at a flow rate of 8 SCFM at 80 psi operate the robotic heads.

Receiver 64 is mounted with an electrostatic-vacuum chuck 68 as described, by way of example, in the aforementioned application "Apparatus for Clamping a Planar Substrate, Ser. No. 09/095,321 filed Jun. 10, 1998 by Sun et al., APPARATUS FOR CLAMPING A PLANAR SUBSTRATE. Vacuum lines, power lines and sensor monitoring lines(not shown) are mounted to the receiver 64 to provide operating resources for the chuck. Where substantial number of lines are to be fixed to the receiver 64, the robots are selected or modified to accommodate the additional weight.

The platform 26 is framed by supports 66 to which the walls 28 are secured. The atmosphere within the platform 26 may be air or an inert gas.

The receiver 64 has circuitry which controls and operates the chuck 68. FIG. 11 shows the upper surface of electrostatic chuck 68 with through spaced holes ECH that are either slots or linear arrays of small apertures that mimic a slot. The holes ECH extend about the periphery of the chuck 68 in spaced arrays as shown. Other configurations for the through holes ECH are illustrated in the aforementioned application Ser. No. 09/095,321 filed Jun. 10, 1998 by Sun et al., APPARATUS FOR CLAMPING A PLANAR SUBSTRATE. Powder/grain collection zones CZ formed by electrodes are located on surface 70 otherwise composed of dielectric material.

Figure 12:
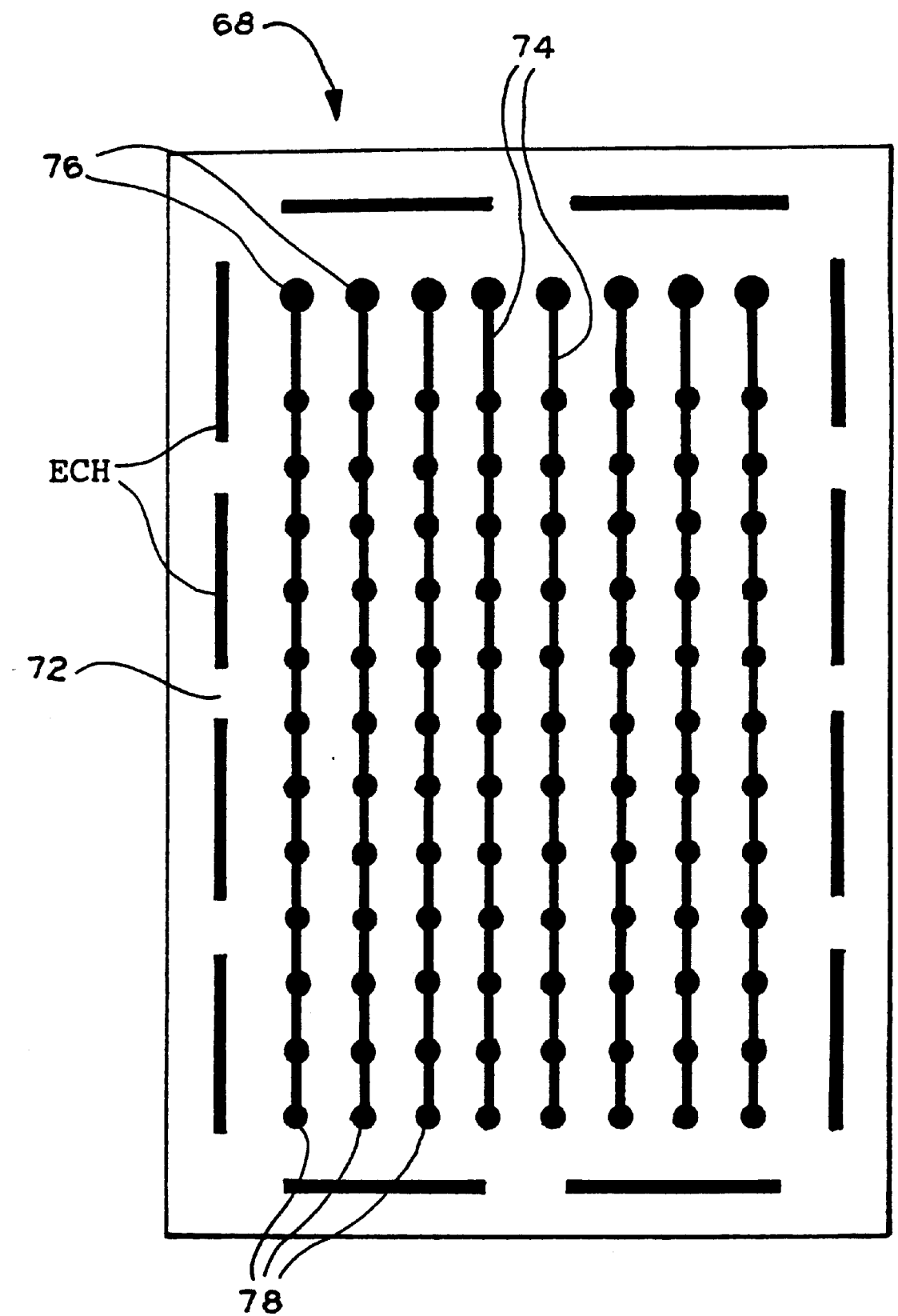
FIG. 12 is a plan view of a rear surface of the chuck of FIG. 11 showing addressing electrodes coupled to drive electronics (not shown) for driving powder collection electrodes.

FIG. 12 illustrates a rear surface 72 of the chuck 68 which has addressing electrodes 74 through which each row of the electrodes forming the collection zones CZ can be connected by driving electronics (not shown). Electrical contact pads 76 provide contact points for connections to voltage sources for controlling the amount of powder/grains deposited at each collection zone CZ.

The pads 76 and collection zones CZ (FIG. 11) connected by the electrodes 74 are arranged in eight columns 78 of 12 collection zones each, for example, each collection zone corresponding to a deposition location on the base substrate 6 (FIG. 1). Each contact 76 can receive a voltage independently of the voltage of the other contacts to separately control the amount of powder/grains deposited on the collection zones of a given column. The addressing electrodes can be arranged in different patterns to allow different control patterns. The voltage on each contact creates an electrostatic field at the corresponding electrodes at the collection zones CZ. This field attracts the powder/grains of active ingredient to the associated base substrate 6 and also holds the substrate 6 flat against the chuck.

Figure 15A:
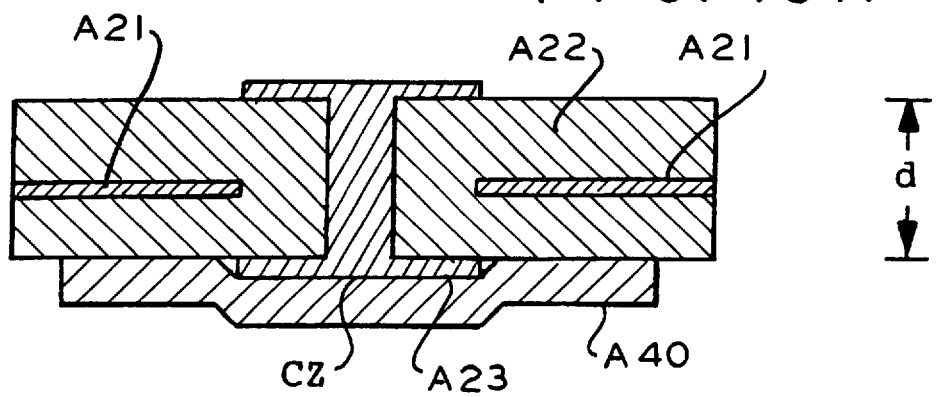
FIGS. 15a, 15b and 15c are schematic sectional elevation views of different embodiments of powder/grain attracting electrodes that may be employed in the electrostatic chuck embodiment of FIGS. 7, 8, 11, 12 and 13.
Figure 15B:
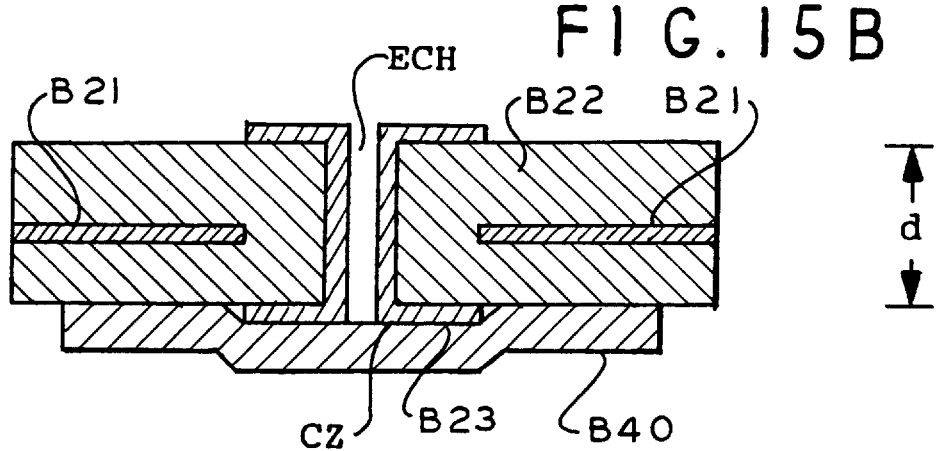
Figure 15C:
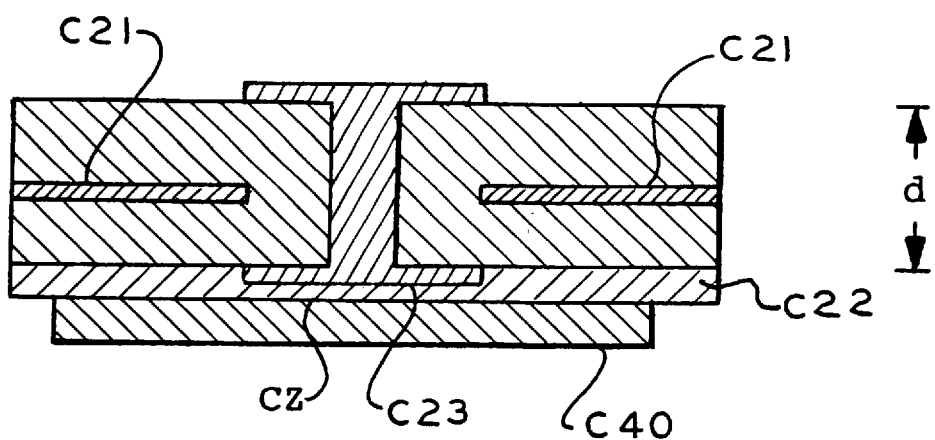

FIGS. 15A–15C illustrate features of electrostatic chucks at a collection zone CZ that can be employed in the present invention. In FIG. 15A, a shield electrode A21 (also termed a "ground electrode" based on a preferred bias) is layered with a dielectric A22 which dielectric can comprise, for example, Kapton, a registered trademark of DuPont de Nemours for a polyimide film. Kapton material can be etched, punched and laser drilled and used to form multi-layer polyimide film laminates.

The powder/grain-attracting electrode A23 projects out at the surface that attracts the planar substrate A40, for example 0.001 inches thick (0.0254 mm), and can project out at the opposing side where electrical contacts are formed. The width d of the film dielectric A22 forming the chuck can be 0.01 inches (0.254 mm) for example. This makes the chuck 68 relatively flexible. The planar substrate A40 wraps over the outwardly projecting powder/grain-attracting electrode A23 in relatively close fitting relationship. This is most effective when a vacuum chuck is used in conjunction with the electrostatic chuck. That is, a vacuum is applied directly to the substrate via apertures (not shown) in the chuck to hold the substrate flat against the chuck. As described, the grain attracting electrodes play a role in adhering the planar substrate to the chuck. Tight adherence of the planar substrate to the electrostatic chuck increases the reliability of powder/grain deposition at the collection zones.

FIG. 15B illustrates an embodiment where the through holes ECH are formed at the powder/grain-attracting electrode A23. FIG. 15C illustrates an embodiment where an additional layer of dielectric C22 separates the powder/grain-attracting electrode C23 from the planar substrate C40. The chuck of FIG. 15C can be termed a "Pad Indent Chuck" which is useful, for example, for depositions of less than about 100 mg per collection zone CZ (assuming a collection zone of about 4 mm diameter). The electrostatic chuck provided by the configuration of FIG. 15A can be termed a "Pad Forward Chuck" which is useful, for example, for deposition so more than about 20 mg per collection zone CZ, assuming a collection zone of about 4 mm diameter, but which is more useful for higher dose depositions than the Pad indent Chuck.

In FIG. 7, the receiver 64 preferably comprises an electronics housing 78, a vacuum manifold housing 80, and a gasket 82. The chuck 68 is preferably aligned with the receiver 64 with locating pins and alignment holes. The vacuum manifold housing 80 has passageways 84 which convey reduced pressure to the through holes ECH (FIG. 11) in chuck 68. Reduced pressure is applied to the passageways 84 via inlet fitting 86, and via passageway outlet (not shown). Because the chuck 68 is flexible, and therefore, susceptible to deformation, and because it can be important to deposit powder/grains on a flat surface, a mechanism is provided to couple the powder/grain attracting electrodes to a voltage source without applying significant distortion pressure to the chuck 68.

Coupled pins 88 provide this mechanism. Lower pin assemblies 88', FIG. 8a, of the coupled pins 88 are inserted thorough holes in electronic housing 78, the vacuum manifold housing 80, and gasket 82, with a conductive adhesive, such as silver epoxy, on the lower part of the lower pin assemblies 88', FIG. 8a. The lower pin assemblies 88' have a notch 90, FIG. 8b, to allow excess adhesive to relocate in the holes. The adhesive adheres the lower pin assemblies 88' to the electrical contact pads 76, FIG. 12. The upper parts of the coupled pins 88 are standard circuit board pins, which couple with slots (not shown) on pin connector board 94, FIG. 8.

Gasket 82, FIG. 9, has slot holes 96 which allow reduced pressure (e.g., vacuum) to be transmitted to the electrostatic chuck 68 through holes ECH, FIG. 11. Another set of conduit holes 98 allow the coupled pins 88 to be inserted through the gasket 82. The gasket 82 insulates preferably at least about 2000–2500 volts and in one embodiment is coated on both sides with an adhesive. A graphics art paper meeting these requirements, which is of 0.004 inches thickness (0.1 mm) and coated on both sides with an aggressive rubber-based adhesive is available from Cello-Tak, Island Park, N.Y.

The receiver 64 may be manufactured from a durable non-conductive material such as a Noryl polymer (A registered trademark of GE). Noryl engineered plastics are modified polyphenylene oxide, or polyphenylene oxide and polyphenylene ether, resins. The material is modified by blending with a second polymer such as polystyrene or polystyrene/butadiene. A variety of grades are produced by varying the blend ratio and other additives. The material exhibits strong intermolecular attraction with extreme stiffness and lack of mobility. The Noryl based support provides firm support for maintaining a flat surface collection zone CZ containing surface of the electrostatic chuck 68 while the low weight reduces the burden on the robotic heads of robots 46 and 56 (FIG. 1a). The surface of the receiver 64 on which the electrostatic chuck 68 is mounted is preferably flat to +/−0.001 inches for example.

Figure 13:
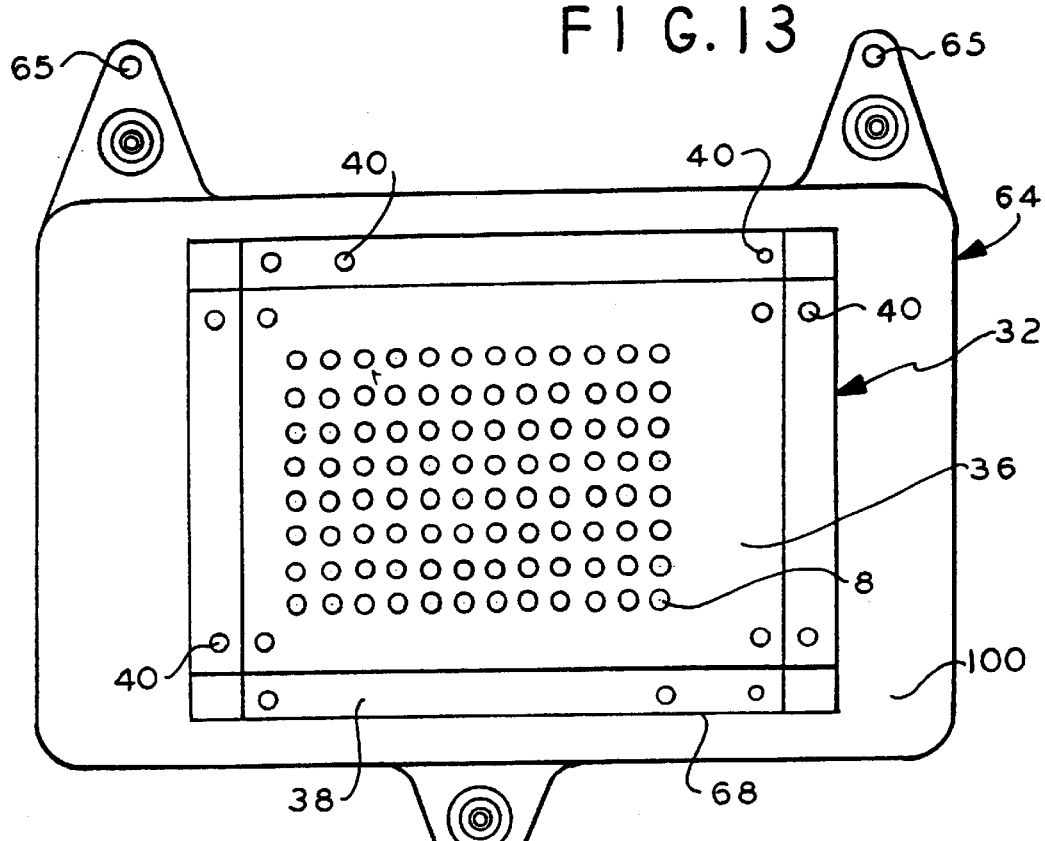
FIG. 13 is a plan view of the underside of the chuck attached to a robotically operated receiving head.

The frame 38, FIG. 13, for the substrate is employed for securing the substrate aligned to the various stations and robotic heads of the system. The frame is also used to hold the substrate to the chuck 68 via the chuck vacuum holes ECH, FIG. 11. The vacuum releasably secures the frame 38 to the chuck by the applied vacuum from the receiver 64. The frame 38 is preferably aluminum. The frame may be about 200 mm by 300 mm with sides having 12.7 mm width. Vacuum cup receiving fixtures on the frame 38, height adjustable vacuum cups (not shown) and vacuum fittings (not shown) on the receiver 64 may also be employed to hold the frame to the chuck.

Figure 14:
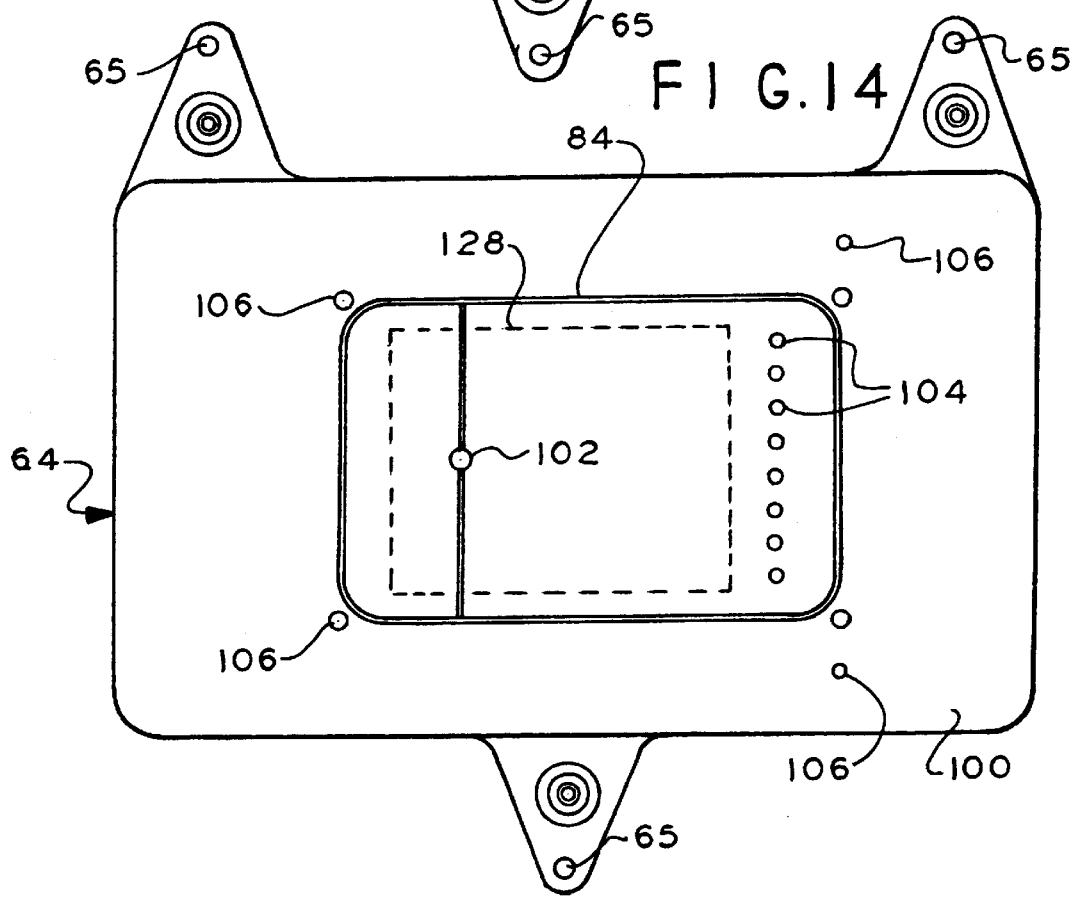
FIG. 14 is a plan view of the receiving head without the chuck installed.

FIG. 13 shows the chuck 68 adhered to the underside 100 of the receiver 64. Electrostatic chuck 68 has alignment mechanisms 40 which may comprise pins or holes for aligning the chuck to the receiver 64 with mating pins or holes. In FIG. 14, receiver underside 100 is shown without the chuck 68, showing passageways 84 and outlet 102 along with pin 88 conduits 104. Alignment mechanisms 106 are shown and can be pins or holes which mate with holes or pins in the chuck 68.

Electronic control is integrated in the dry powder/grain deposition apparatus 60. This control is coupled to a processor board (not shown) in the receiver which functions as a communication board. This board receives commands from the central processor in controller 62 (FIG. 1a) and relays these commands to an addressing circuit board (not shown) in the receiver 64. Also, in some embodiments, an embedded processor circuit board (not shown) in the receiver 64 receives data from sensors positioned on or adjacent to the electrostatic chuck 68 and interprets locally any adjustments to the voltages applied to the powder/grain attracting electrodes A23–C23 (FIGS. 15A–15C) that are appropriate in view of this data. These sensors are described below.

The addressing board, after receiving signals from an on-board processor board (not shown-on the receiver 64) sends bias control signals, DC or AC, e.g., about 2000 V at low current, for controlling the voltage at the electrodes 76, FIG. 12. This thus applies the voltage to the powder/grain-attracting electrodes A23–C23, FIGS. 15A–15C, in individual columns 78 or rows of electrodes or individual rows of electrodes according to a given implementation. In FIG. 12, the addressing electrodes 74 allow control individual columns of powder/grain-attracting electrodes at the collection zones CZ, FIG. 11.

The bias signals from the addressing board can be used to separate columns or rows of powder/grain attracting electrodes, or to individual powder/grain attracting electrodes. Such adjustment can be made, for example, where sensors as described below, or data from the dose measurement station 50 based on a previous deposition, indicate that an uneven distribution of deposition amounts is occurring. As a result, the voltages at the collection zones CZ may be advantageously increased or decreased accordingly.

The chuck 68 of FIGS. 11 and 12 has addressing electrodes 76 that allow control of individual columns of powder/grain attracting electrodes A23–C23 (FIGS. 15A–15C). Electrical signals manifesting control patterns that control regions or individual collection zones CZ can also be used.

The addressing board preferably has multiple channels of synchronized output signals, e.g., square wave or DC. These signals may be encoded with square wave pulses of varying magnitudes to identify the powder/grain-attracting electrodes or group of electrodes together with the appropriate voltage to be applied for controlling the amount of powder/grains to be deposited. The bias control signals are sent via a high voltage board (not shown) in the receiver 64 which has multiple channels of high voltage converters (transformers or HV DC-to-DC converters) for creating the deposition control voltages, such as 200 V or 2,500 V or 3,000 V (of either polarity), for operating the powder/grain-attracting electrodes. By forming the higher voltages within the receiver 64, these high voltages can be isolated from other systems.

The central processor unit controller 62, FIG. 1a, receives performance input from multiple sources. This input provides data on the rate of particle flux into and through the deposition engine comprising feed apparatus 60 (FIG. 1a) and deposition station 52, how evenly particles are being deposited at the chuck 68 and how well previous depositions have met the required thickness values. Various parameters of the system may be adjusted in view of this data, including voltages at various locations on the chuck to improve performance. The on-board electronics at the receiver 64 provides the means to make these adjustments on-the-fly to be conveyed to the powder/grain attracting electrodes 74, FIG. 12.

A charge sensor 128, FIG. 14, is on the receiver 64 for sensing the amount of charge on the powder/grains attracted to the electrodes A23–C23. The sensor 128, which is schematically represented by the dashed lines, monitors the amount of powder/grains deposited, and is described in detail in the copending application Ser. No. 09/095,425 now U.S. Pat. No. 6,149,774 noted in the introductory portion. This application describes the use of pulsed (AC) electrical potential waveforms for biasing an electrostatic chuck to collect powder/grains such as on a substrate. This biasing overcomes the problem of collecting the powder/grains on a conductive substrate, where the powder/grain-attracting field can decay rapidly after any given application of a bias potential to the electrostatic chuck.

The use of AC bias waveforms for the powder/grain attracting electrodes also solves another long-standing problem during deposition sensing. During deposition sensing, one or more collection zones are closely monitored for powder/grain accumulation to allow regulation of the deposition process, to produce, for example, precise pharmaceutical dosage or diagnostic dosage unit amounts. This monitoring can be done optically or by measuring accumulated charge using an "on-board" charge sensor at a sensor associated collection zone, which can be correlated to actual charged grain deposition by empirical data collection. In dry powder/grain deposition, for example, dose monitoring is often a difficult task, particularly for dosages below one milligram.

The difficulty is not that measuring devices are not available—modern solid state devices, although costly, can make measurements so precise that noise levels are on the order of the voltage generated by the charge of a few hundred electrons. Rather, the difficulty lies with various practical and environmental factors that deteriorate charge sensing sensitivity by two or three orders of magnitude. For quasi-static DC biased bead (deposited powder/grains) transporter chucks, on board charge sensing is particularly difficult. Data obtained by depositing on a polypropylene film substrate with different potentials indicates that the deposited dose is linearly related to the bias potential if that potential is above a certain threshold potential. Data indicates that threshold potential is about 100–200 volts DC, at least for certain transporter chucks.

Figure 20:
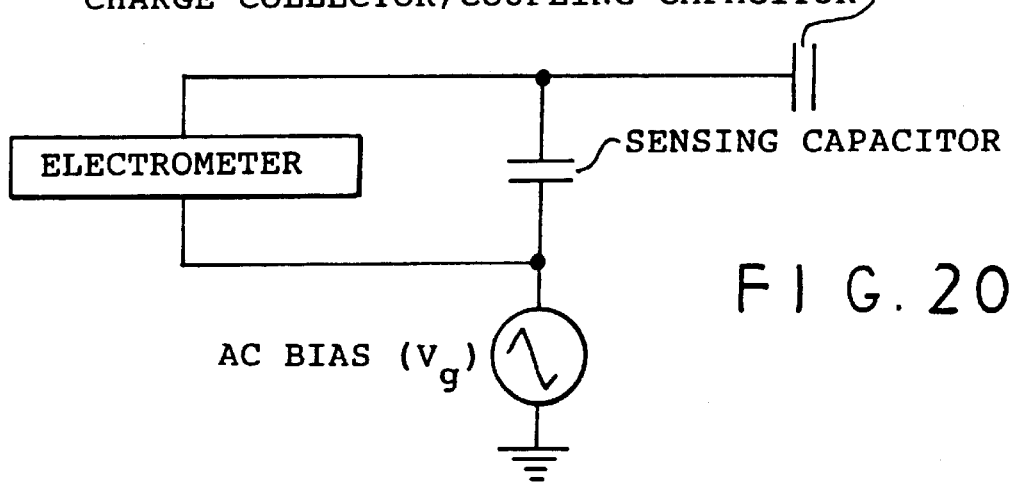
FIG. 20 is a schematic circuit diagram for providing an AC bias charge and deposition sensing for a floating pad electrode.

In FIG. 20, one possible equivalent circuit diagram for the circuit provided by the electrostatic chuck and substrate is illustrated. The chuck and substrate corresponding to this equivalent circuit includes a planar bead electrode that is used to provide a bead attracting field. Affixed to the bottom face of the bead electrode is a planar first dielectric layer. The dielectric layer is applied to or affixed to the bead electrode in parallel using any known techniques such as laminating, powder deposition or thin film deposition. Dielectrics may include Pyrex 7740 glass (Corning Inc.) or polyimide resin of 10–20 mils thickness. A planar shield electrode is affixed to the other face of the first dielectric layer. The latter shield electrode comprises an aperture to accommodate a floating pad electrode, coplanar with and surrounded by the latter shield electrode.

The equivalent circuit provides AC biased charge and deposition sensing for at least one of the collection zones, which zone has a floating pad electrode. The floating pad electrode is an isolated conductor which is capacitively coupled to a powder/grain attracting electrode, such that the bias to the attracting electrode indirectly creates a powder/grain attracting field emanating from the floating pad electrode. One or more collection zones are typically dedicated solely for sensing or are in general use, but closely monitored. By measuring the lowering of the attracting potential $V_{CZ}$ that occurs as charged powder/grains collect on the collection zone, a measure of deposited charge can be obtained. By knowing the average charge/mass ratio q/m of the powder/grains, the accumulated deposition mass can be measured. $V_{CZ}$ can be measured directly across a charge collector electrode, but is often preferable to measure the potential across a coupling capacitor, such as the floating pad electrode discussed above.

Figure 21:
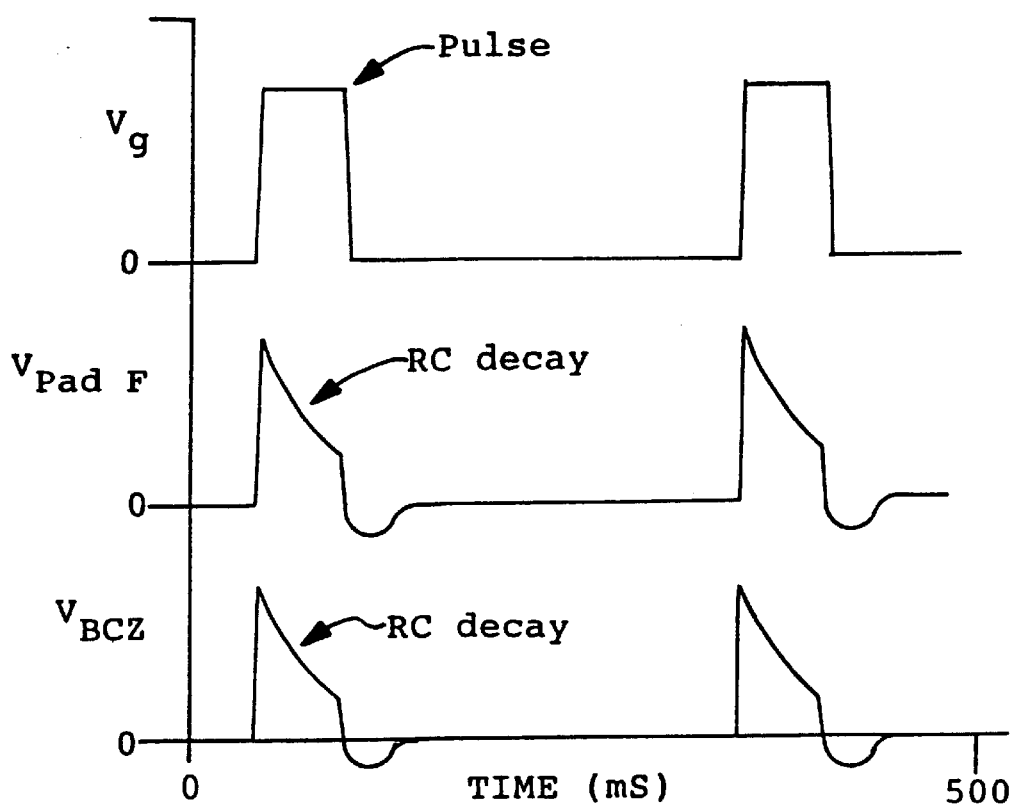
FIG. 21 is a waveform diagram useful for explaining the principles of the diagram of FIG. 20.

The coupling capacitor as embodied by a floating pad electrode described above will provide reasonably high fidelity reproduction of the potential at the collection zone CZ on the powder/grain contact surface, and in FIG. 21, the waveforms for $V_{CZ}$ and $V_{Pad}$ show this. In either case, whether a charge collector or charge coupling capacitor is electrically connected to a separate sensing capacitor, the voltage generated across the sensing capacitor can be a reliable indicator of the potential $V_{CZ}$.

The voltage across the sensing capacitor is measured with an electrometer, such as a Keithly model no. 614, 6512, 617, 642, 6512, or 6517A electrometer as schematically shown in the figure. Generally, the coupling capacitor is any electrode that is capacitively coupled to a collection zone on the contact surface.

A problem is that DC biasing can cause a steady drift in the reading of the potential across the sensing capacitor. This drift comes from many sources, mostly from natural leakage across the dielectric material in the sensing capacitor, and because of charge leakage in the substrate or grain composition accumulated on the chuck. Drift can also be induced by noise factors such as shot noise, Johnson (1/f) white noise, thermal noise, Galvanic noise, triboeleectric noise, piezoelectric noise, amplifier noise, and electromagnetically induced noise. See ref. *The Art of Electronics,* by Paul Horowitz, Winfield Hill, 2nd Edition, Cambridge University Press, 1989, ISBN 0521370957.

If this drift is too large compared to the actual charge collected at the collection zone, the accuracy of the charge sensor as a dose or deposition measurement tool can be unacceptably low. Using AC biased waveforms as disclosed herein will minimize the creation of drift, in a manner similar to that used above for avoiding the "drift" of charge dissipation on the collection zone, allowing precise measurement of charge collected.

In FIG. 20, an AC bias source may be the same source as discussed above, with the AC bias potential applied or administered via the powder/grain attracting electrode. This in turn electrically couples to the floating pad electrode or to the collection zone, if it is connected directly to the sensing capacitor as shown.

For example, if the sensing capacitor is chosen to be 0.1 iF and the q/m of the powder/grains is 10 iC/g, a 100 Mv signal change on the charge collector/coupling capacitor corresponds to 3 mg of powder/grain in the actual deposition dose, then a 99 mg actual dose will have a detectable potential change of 3.3 Mv. With a 5% error tolerance, the corresponding background unpredictable noise contribution cannot exceed 160 iV. This is achievable with careful shielding and grounding. Preferably the charge collector is integrated with the chuck to assure a consistent correlation.

In effect, the same benefits gained by using the AC bias waveforms for $V_g$ to avoid charge dissipation in the substrate can be used to greatly reduce drift in the charge sensing circuit.

Figure 22:
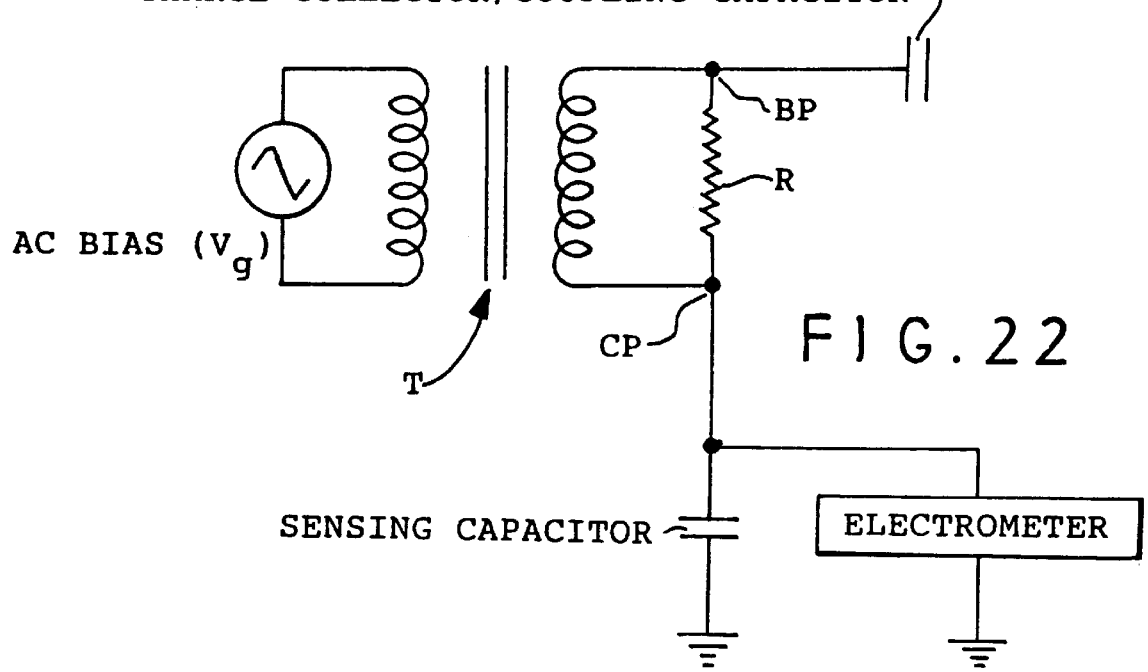
FIG. 22 is a schematic circuit diagram for providing an alternative AC bias charge and deposition sensing.

In FIG. 22, a further possible equivalent circuit provides AC biased charge and deposition sensing. This circuit reduces noise by separating the AC bias source from the electrometer, the sensing capacitor or the charge collector/coupling capacitor. All of these components have a sensitivity to noise that is critical. The AC bias source is connected to the primary of a transformer T. In this manner, only the periodic magnetic field generated by $V_g$ (not $V_g$ itself) is introduced into the sensitive components on the right side of the figure. The secondary winding of transformer T is connected across a stabilizing bleed resistor R, with one pole, biasing pole BP connected to the charge collector/coupling capacitor, and the other pole, at the sensing capacitor, is connected to ground. The electrometer can then measure the voltage change on the sensing capacitor with respect to ground, as shown.

These two grounding points can be combined to reduce electromagnetic noise further. The transformer can be a step-up transformer as discussed so that complex AC bias waveforms supplied here and to the grain attracting electrode can be generated at low cost. For example, the step-up ratio can be 50. This greatly reduces drift and makes accumulated charge sensing more accurate, where previously the coupling current of 100 pico-Amperes or less made drift and noise a problem.

If desired, transformer T can be an isolation transformer, where the primary and secondary windings are separated by a Faraday cage. This can prevent coupling between the primary and secondary windings, where the primary winding acts as one capacitor plate, and the secondary as the other capacitor plate.

With this improved signal to drift ratio, the amount of charge sensed can decrease substantially. Measurements can be made using a 1000 picoF capacitor as the sensing capacitor instead of the 0.1 $\mu$F value used previously. Also, the AC bias source, FIGS. 20 and 22, can be separate from the AC waveform bias $V_g$ on the chuck, by delivering a separate AC bias to the charge collector/coupling capacitor directly, via a dedicated wire, electrode, bus, etc. This separate AC bias can be frequency matched or detuned with respect to $V_g$ to insure consistent correlation of the behavior of the charge collector/coupling capacitor to actual depositions.

Overall, too, these techniques allow $V_g$ biasing with voltage peaks much higher than previously possible. Using 8000 molecular weight polyethylene glycol as a substrate, bias peaks of 2 kV have been used. It is important also to keep in mind that any kind of powder/grain (bead) transporter chuck can be used, including those that operate with bias electrodes directly exposed to the powder/grain (bead) contact surface.

The substrate of assembly 34 must be kept flat during deposition. To do this electrostatic forces may be applied to the dielectric layer A22, for example, FIG. 15A, of the chuck to hold the substrate layer against a reference surface on the chuck. In the alternative, vacuum ports, not shown, may be used to hold the substrate dielectric layer flat. See the aforementioned application Ser. No. 09/095,321 filed Jun. 10, 1998 by Sun et al., APPARATUS FOR CLAMPING A PLANAR SUBSTRATE, for example. This flatness of the layer A22 is important in order to control the thickness, and thus the volume, of the deposited powder/grains to the desired range.

It is important, for example, that the deposited powder/grains at collection zones CZ, FIG. 11, do not vary from a predetermined amount by more than about 5%. While this value may vary somewhat depending upon the drug or diagnostic agent being deposited, generally the value of about 5% variation from a predetermined amount of deposited powder/grains is sufficient for most applications. While such variation might be exceeded in the actual deposition of the powder/grains, the measurement station provides non-destructive actual measurements of the amount (i.e., the thickness over an area) of the powder/grain layers deposited at each of the collection zones CZ.

These values are stored in memory and displayed (by display not shown) so that any unit dosage or diagnostic forms that exceed or are less than the desired range can be selectively discarded. In the present embodiment, a particular column of deposited powder/grains would be identified and discarded at a later processing step if any of the zones of that column are out of the desired range.

The deposition engine may be any known process for depositing the powder/grains. The engine disclosed in the aforementioned application Ser. No. 09/095,246 now U.S. Pat. No. 6,063,194 is preferred. However, the deposition processes of the aforementioned U.S. patents and applications may also be used. The deposition in the former feeds powder/grains through an induction tube to which a bias is applied. This bias provides a charge of the desired polarity on the powder/grains. The tube is of a length sufficient to charge all of the expected powder/grain particles flowing therethrough to the deposition station 52. The particles flow into the chamber 69 via a nozzle (not shown).

The particles pass through an electrified metal control grid (not shown) that has a polarity of the charge on the powder/grains to repel the powder/grains. The grid is about 0.5 to 1.0 inches below the target, and biased about 500 volts per ½ inch at the polarity of the powder/grains. This action collimates the powder/grains as they are propelled upwardly toward the overlying chuck by the electrostatic forces on the chuck and toward the attached substrate 6 then receiving the powder/grains.

The grid also attracts the powder/grains with the wrong polarity. The grid may be parallel wires formed of a zig-zagging switchback of one wire or a grid of wires (not shown). The rate of powder/grain cloud of powder/grain flux can be monitored by measuring light attenuation between a light emitter (not shown), e.g., a laser, and a light detector (not shown). This value is transmitted to the controller 62, FIG. 1*a*.

A rotating baffle (not shown) is coupled to the nozzle (not shown) outlet in the deposition station 69 to disperse the powder/grains prior to the grid to more uniformly apply the powder/grains to the substrate 6. The baffle may comprise three equally spaced radially extending rotating planar baffle supports (not shown) on which rests a horizontal baffle disk (not shown) through which are a plurality of powder/grain aperture outlets. The powder/grains are fed to the nozzle with a gas at about 20 psi and about 2.5 liters per minute. The gas is preferably substantially free of water, oil and other impurities, and is preferably chemically inert such as nitrogen or helium.

The baffle should be preferably about ¼ inch to about ½ inch above the outlet of the powder/grain charging feed tube nozzle such as ½ inch cross section where a ¼ inch powder/grain charge feed tube nozzle is used. Rotating the baffle at about 5 to 25 revolutions per minute increases the uniformity of the powder/grain cloud reaching the target.

The powder/grains may be fed by an auger (not shown) rotating, e.g., 10 to about 80 RPM, to feed the powder/grains to a Venturi feed valve (not shown). The auger is supplemented by the powder/grain Venturi feed tube which pulls the powder/grain from the auger and at the same time pushes the powder/grains through the feed tube to the nozzle at the chamber 69. A modified Venturi feeder valve with a Venturi well that delivers grains in a substantially straight line from the vertical auger feed to the powder/grain charging feed tube avoids compaction of the powder/grains falling to the bottom of the Venturi well. A simple gas source may be used in place of the Venturi to propel the powder/grains. A gas jet directs gas pressure toward the outlet of the mechanical device that feeds the powder/grains, the gas jet being adjusted to deagglomerate the powder/grains at the outlet.

Nitrogen may be used to feed the powder/grain particles via the venturi. The auger and feed tube connected to the auger through a venturi valve are vertically aligned. A vibrator (not shown) coupled to the feeding apparatus is preferable to keep the particles flowing. Other grain feed arrangements may also be used such as a gear wheel apparatus (not shown) or a jet mill (not shown) for dosages of about 2 ig to about 50 ig–100 ig applied to an area of about 3 to 4 mm diameter.

Induction induced charge may be applied to the jet mill by applying a potential to the mill such as with a 1,800 V potential. A suitable mill may be a TROST Air impact Pulverizer jet mill marketed by Plastomer Products Division of Coltec Industrial Products, Inc. This mill utilizes directly opposing streams of compressed gas and operates at a flow rate of about 2.0 to 2.2 liters/minute.

The powder/grains may by charged by triboelectric charging, the charge to the powder/grains colliding with the sides of its feed tube as the powder/grains transit the tube. Teflon, perfluorinated polymer may be used to impart a positive charge to the powder/grains and Nylon, amide based polymer, is used to impart negative charges. To minimize charge build up on the tube, the tube may be wrapped in metal foil or coated with conductive material such as graphite.

In the induction charging, a portion of the feed tube is stainless steel biased by one pole of a power supply with the opposite pole grounded. With an appropriate bias, an electric field is created in the stainless steel tube such that powder/grains passing through it pick up a charge. The length of the induction-charging tube is set to a sufficient length to assure the amount of charging desired. In one embodiment, induction charging is used in conjunction with tribocharging.

The charge relieved by the grounding procedures outlined above can be monitored to provide a measure of powder/grain flux the charging feed tube (not shown). This data can be sent to the controller 62 (FIG. 1*a*) to modify various parameters of the deposition apparatus. For example, a capacitor (not shown) can be put in series with the powder/grain charging feed tube to lower the potential generated by the charges collected in the charging feed tube. A 1 iF capacitor will build up 1 V for a 1 iC charge. The other pole of the capacitor is connected to ground potential. An electrometer (not shown) connected to the capacitor provides an accurate measure of collected charge.

Powder/grains not utilized at the deposition station are returned via a pressure differential through a powder/grain evacuation tubes (not shown) to a powder/grain trap (not shown). The trap utilizes biased baffles biased at for example either +2000 V or −2000 V. Grains not charged are charged by impact with a baffle of one polarity and collected by an oppositely charged baffle.

Shutdown of the deposition process for example as a result of the feedback data such as from the charge sensor or pursuant to a timing schedule involves reducing the voltage (or the amplitude in the case of a pulsed voltage profile) directed to the powder/grain attracting electrodes, preferably to about 400 V from 2000 V, and shutting down the powder/grain feed apparatus. The amount of voltage reduction appropriate will vary depending upon such factors as the substrate, the powder/grains and the level of the powder/grains applied. The voltage is generally selected to maintain substrate adherence to the chuck and grain adherence to the substrate without attracting further grain accumulations.

The dose measurement station 48 includes apparatus 50 for measuring the thickness, i.e., the amount of powder/grains deposited on the substrate 109. Two optical measurement methods may be employed: diffuse reflection and optical profilometry. Diffuse reflection has been used to characterize powder/grains using light sources that emit in a range that is absorbed by the powders. A theory has been developed for using non-absorbing radiation which derived a term for the thickness of a powder/grain layer. It is believed that no commercial development has been made from this latter theory. Applicants have discovered that this measurement gives a strong correlation with the deposited amount, at least up to a certain amount, which varies with the character of the powder/grain/grains and are believed to correspond to amounts past which light penetration into lower layers is prevented.

Diffuse reflection is based on the reflection or scattering of a laser beam or a probe light beam off of the powder/grain surface into directions that are not parallel to the specular reflection direction. This scattered light is generally uniformly distributed in all directions. Dose depositions which exhibit this property are said to be "Lambert radiators," an important property for dose weight measurements.

In addition, the relation between the Lambertian scattering and the optical properties of powder/grains is defined by the scattering model of Kubelka and Munk. Non-absorbing radiation is used to create diffuse reflection. Typical radiation is the visible red lines provided by common gas and diode lasers such as 732.8, 635 and 670 mm. When non-absorbing radiation is used and when the dose deposition is of a finite thickness, d, the Kubelka -Munk model provides a known relation as disclosed in the aforementioned application Ser. No. 09/095,246. U.S. Pat. No. 6,063,194.

Figure 16A:
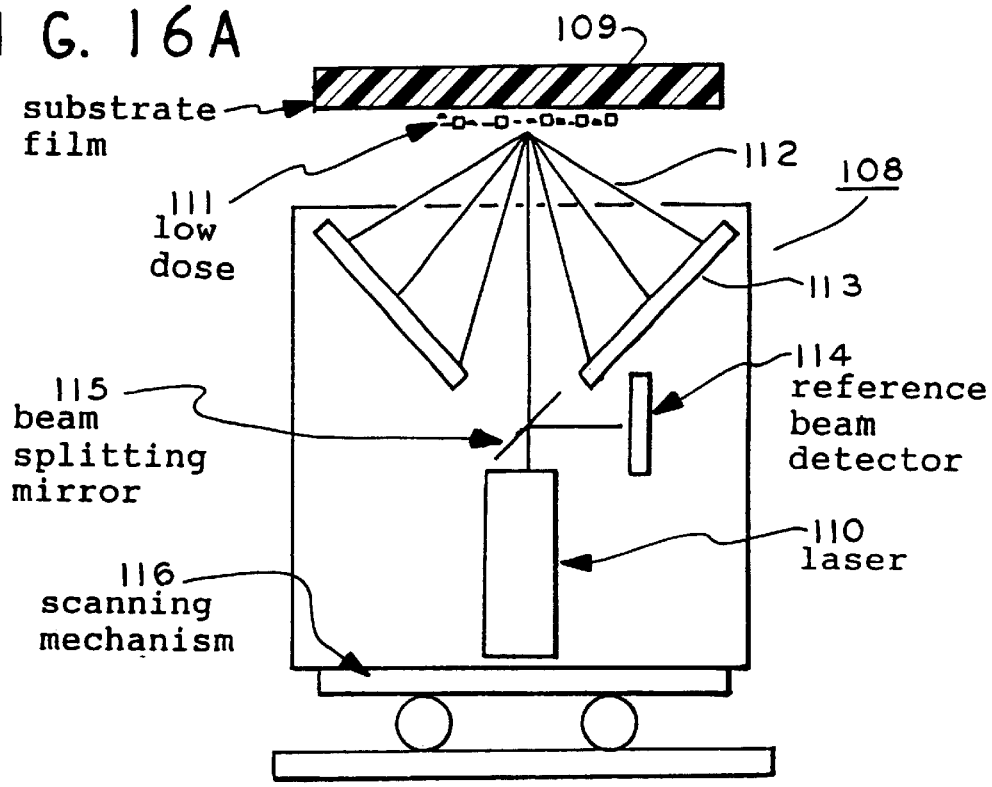
FIG. 16A is a schematic illustration of a diffuse reflection system for characterizing the amount of deposited dry powders.

In FIG. 16a, a diffuse reflection measurement apparatus 108 includes a laser 110. When a low energy beam from laser 110 impinges on deposited particles 111, the particles scatter LHT in all directions. To have a coherent laser, it is desirable that the laser be focused through beam splitting mirror 115. a reference beam detector 114 assists in determining the quality and intensity of the focused beam. The scattered light LHT is captured by an array of two or more detector zones 113. There can be for example 2 to 6 or more such zones. Amplifiers (not shown) may be used with the detectors. The detector zone outputs is connected to a commercial A/D converter (not shown). The resulting signal is scanned by using a computer controlled scanning mechanism 116, which is in communication with the central electronic processor of controller 62, to generate powder/grain thickness profile and thus the dose weight measurements of the depositions.

It is preferred the powder/grains be deposited on a substrate that has a specular surface and the substrate be absorptive so that the measurement will not be sensitive to diffuse reflections off of its back surface or off of the surface of the receiver 64.

Diffuse reflection in non-absorbing regions provides a good accuracy in measuring dose deposition amounts ranging from 50–400 ig or as high as 750 ig to 1 mg. for a 3 or 4 mm diameter powder/grain deposited dot depending upon powder/grain characteristics. The powder/grain dots may have a diameter of about 4–7 mm in this embodiment. This method can detect substantially less than a monolayer of powder/grain.

If the deposit is more than a monolayer, accurate measurement requires that the probe light beam partially penetrate the upper layers so that it can be affected by the reflection off of the lower layers. However, to exhibit Lambertian characteristics, there tends to be a practical limit to suitable thickness, depending on the powder/grain. The diffuse reflection is also a measure of the physical uniformity of the dose deposits at the above ranging.

Figure 16B:
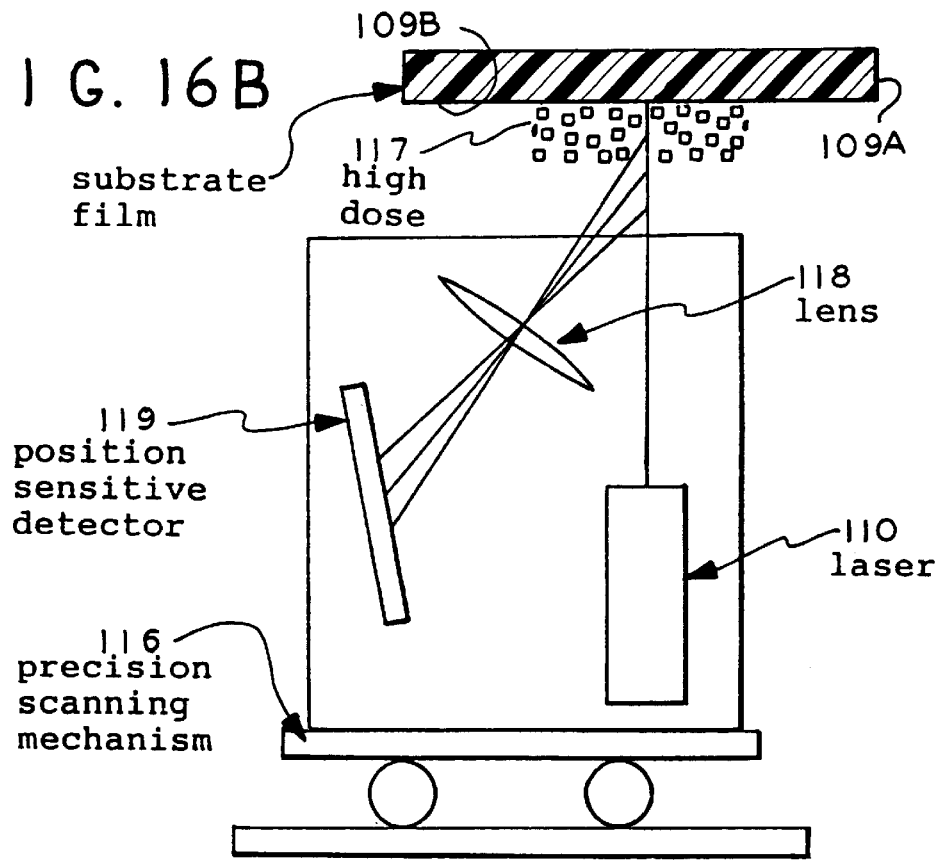
FIG. 16B is a schematic illustration of an optical profilometry system for characterizing the amount of deposited dry powder/grains.

Optical profilometry is useful for the implementation of high dose measurements beyond the ranges that can be measured by the diffusion reflection method. In FIG. 16b, a laser beam is focused on a high dose deposition 117 on substrate 109a. The light is deflected with an angle of deflection indicative of the height of the deposition layer, which can be calculated by triangulation. The coherence of deflected light, which may be somewhat scattered, can be assisted by a lens 118 before the scattered light is captured by one or more position sensitive detectors 119. The output data from the detector is scanned by using a scanning mechanism 116 to generate a profile of the powder/grain surface.

The profilometer can be, for example, a confocal profilometer, meaning light is directed to the substrate through a lens system, and returned light passes at least in part through the same focusing system, though typically the returned light is reflected to a detection site. In one suitable confocal profilometer, a Model LT8105, Keyence Corp., Japan, or Keyence Corporation of America, Woodcliff Lake, N.J. focuses source light through a pinhole, and a similar focusing through a pinhole of the return light helps establish focus. A source of back and forth dithering movement applied to one of the lenses helps establish oscillations in the focus which help identify the optimal focus point.

In one embodiment, a slit can be used in place of a pinhole and a spatially resolvable light detector, such as a charge-coupled device (CCD), is used to simultaneously retrieve data for multiple points along a linear area of the substrate. In some embodiments, there can be an issue of the powder/grain attracting electrode or some other feature of the receiver creating strong reflections that could overwhelm efforts to establish the baseline surface of the substrate. However, since the substrate is preferably uniform, these issues can be normalized away. Once material is deposited on the substrate, or where the substrate is sufficiently opaque, clean reflections can be obtained.

To obtain accuracy by optical profilometry, a pre-dose measurement of the substrate 109a is preferred. The beam is scanned across the surface and the height of the surface from a reference location is established by triangulation. The difference in height from the reference before and after the deposition is calculated. This difference is attributable to the dose weight.

This difference is calculated for each column of collection zones CZ, FIG. 11, and for each collection zone CZ. The controller 62 stores these values in memory and displays the difference as a measure of the dosage amount for each dosage unit. When any of the individual unit dosage amounts is beyond the predetermined amount by the preferred 5% value, those units can be later identified and selectively discarded for each substrate that is produced and measured providing 100% inspection with non-destructive testing of the actual amounts of each unit.

Since dry powders/grains are generally good diffuse reflectors, it is convenient to use an optical triangulation system that is optimized for diffuse reflection. To determine the pre-dose surface profile, and to establish the height of the substrate at issue during the post-dose measurement, it is preferred that the substrate surface 109b be also diffuse. The surface should also be absorptive so that the triangulation system not be confused by reflections from the back surface of the substrate or from the receiving system.

For purposes of illustration, only a single laser 110 is shown. However, more than one laser can be used to impinge on the powder/grain particles in different areas of a deposition site. The scattered light is captured by different detection zones which ultimately are scanned for the desired characterization.

In some embodiments, the deposition sites are excited in succession and the powder/grain profile is characterized after each light source excitation through the scanning mechanism 116 by moving the scanner, for example, from a first site to a second site and so on until all of the deposition sites are characterized.

In other embodiments, more than one deposition site is laser excited at a time and data is obtained by scanning the sites simultaneously. In such situations, it is desirable to optimize conditions for reducing the interference from nearby sites that are being characterized simultaneously. This can be accomplished by, for example, optimizing the spacing between deposition sites or by alternating the excitations of different sites.

It is desirable that the laser be movable in different directions. An industrial process grade (x,y) stage can assist the laser to move in the x,y directions. A solid state laser suitable for industrial applications such as, for example, LAS -200-635-5 from LaserMax Inc. can be used as a laser source. the detectors can be any suitable device, preferably, silicon, detector such as those sold by UDT Sensors, Inc. (Hawthorne, Calif.). alternatively, large area solar cells can also be used.

Figure 17:
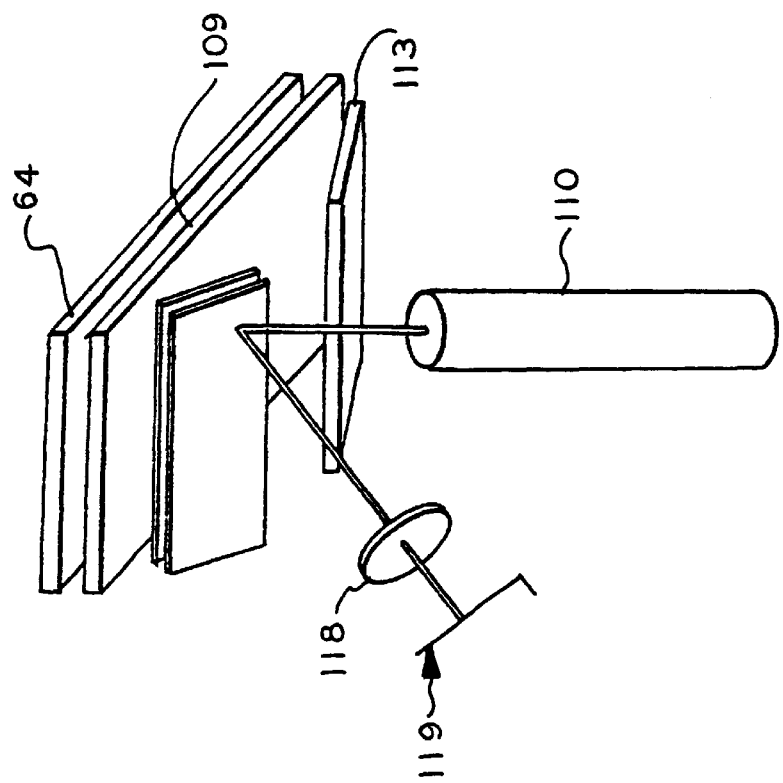
FIG. 17 illustrates a substrate that can be measured with both the optical profilometry and diffusion reflection systems of FIGS. 16B and 16A respectively.
Figure 16A:
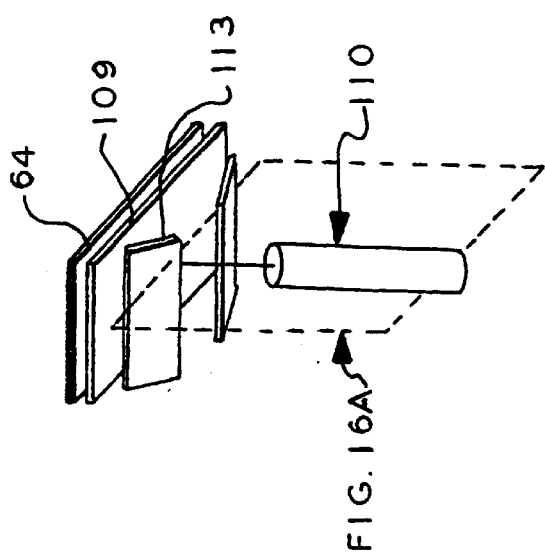
Figure 16B:
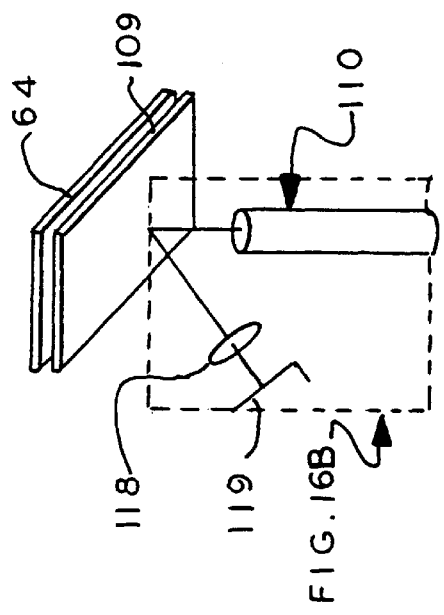

It is often desirable to combine both of the dose measurement systems into a single system so that both the low dose and high dose measurements can be made and the range of the dose measurement is not limited by any single method used. In FIG. 17, substrate 109 is striated and is useful for both the profile and diffuse reflection systems. Striated substrate 109 has surface striations running in only one direction. The surface profile measurements are made by positioning the triangulation system with incident and reflected beams in a plane perpendicular to the striation direction. The striations thus act like a diffuse surface for this measurement. The diffuse reflection measurements are made in a plane that contains the striations.

Ideally, striations do not scatter light in a direction parallel to themselves, so that any scattered light is attributable to the powder/grain on the surface. For both measurements, the substrate can also be dyed so that reflections from the substrate's back surface or from the receiving system's surface do not interfere with the measurement of either the profile or of the diffuse reflection. The system of FIG. 17 combines two modes of measurement with the use of just one light source, while the system of FIG. 19, discussed below, shows a system where measurement modes each have a separate light source.

In embodiments that do not use frames or another mechanism for alignment of the substrate at the deposition station and the measurement station are the same, the dose measurement system is arranged to identify the positions of the depositions. Such a mechanism could be a video camera that collects data, for example, in a charge-coupled device (CCD) and electronics to analyze the contents of the CCD to determine the boundaries of the depositions.

It should be understood that the unit pharmaceutical or diagnostic dosage powder/grains deposited at a collection zone CZ are measured both in area and thickness to provide a volume measure manifesting the amount of powder/grains deposited in a deposited collected powder/grain dot at each zone. The above diffuse and profilometer measurements while described in terms of thickness are also measured in conjunction with areas that are determined by the scanning beams.

Adjacent scan beams are closely spaced, for example 1 mm apart, so that the transverse region occupied by a collection zone CZ is also measured and considered in the calculations of the amount of powder/grains present at each deposited location. The beams are about 6 i(microns) in diameter in this embodiment. For a deposition zone of about 4–7 mm, each deposited powder/grain dot will be scanned with four to seven scans, respectively. These scans are then used to calculate the amount of dosage at each collection zone CZ. The system remembers the calculations for each zone for future selective screening of out of specification of pharmaceutical or diagnostic unit dosage forms.

Polyethylene glycol (PEG) powder, by way of example, in a about 3 mm diameter dot has been deposited onto a Mylar substrate. The diffuse reflectance data was obtained using a laser (670 mm) based Keyence instrument (Keyence Corp. of America) operating in the intensity mode. Data was obtained using different, usually larger, fractions of the diffusely scattered light. The analytical properties of the measurement did not appear to be very sensitive to the fraction of collected light, i.e., the measurement is, in this context, unusually robust and ideal for use as an industrial measurement process.

Figure 18:
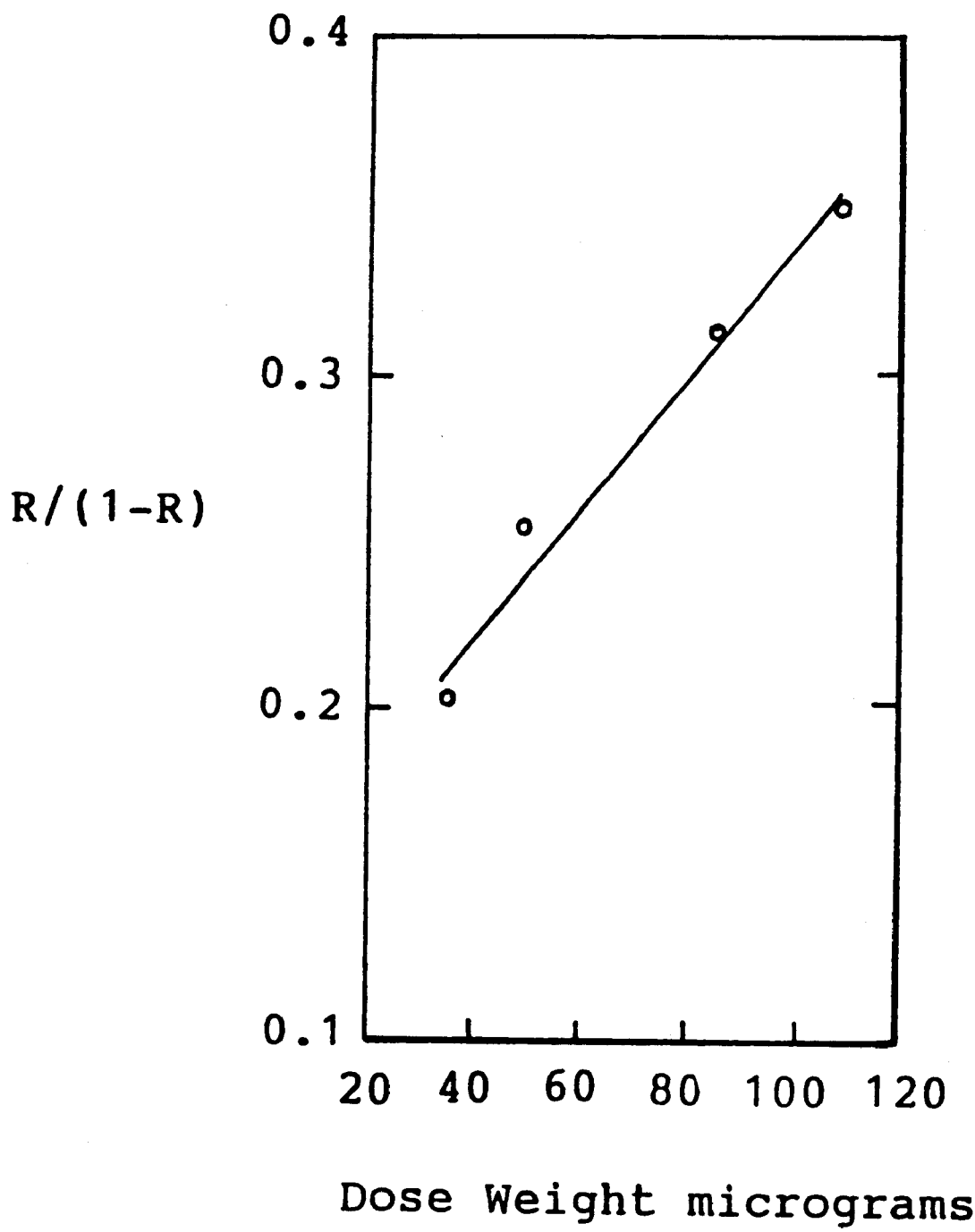
FIG. 18 is a graph useful for explaining the principles of the present invention.

The data set forth in Table I below which was obtained using diffuse reflection method was the basis for the graph of FIG. 18, for the four points of the data set. The first three points were highly correlated and the least squares fit gave an R value, a measure of correlation, of 0.999. Perfect correlation gave a maximum value of R which is 1 and, with less correlation, the value is correspondingly less than 1. The fourth point show variation and the least squares fit for the data set as a whole gave an R value of 0.98. Both R values were well within accepted norms for analytical procedures to determine dry powder/grain dose weights.

TABLE I

Experimental diffuse reflectance and dose weight data

| PEG Dose Weight, Micrograms, by Assay | Calculated R/(1-R) |
|---|---|
| 108.6 | 0.35 |
| 86.6 | 0.312 |
| 50.6 | 0.254 |
| 36.6 | 0.201 |

Subsequent measurements had shown that a high degree of correlation existed for the diffuse reflection and dose weight for various types of dose samples. Based on these data, the degree of correlation is thought to be closely related to the structure of the dose, specifically whether the structure exhibits Lambertian characteristics.

Figure 19:
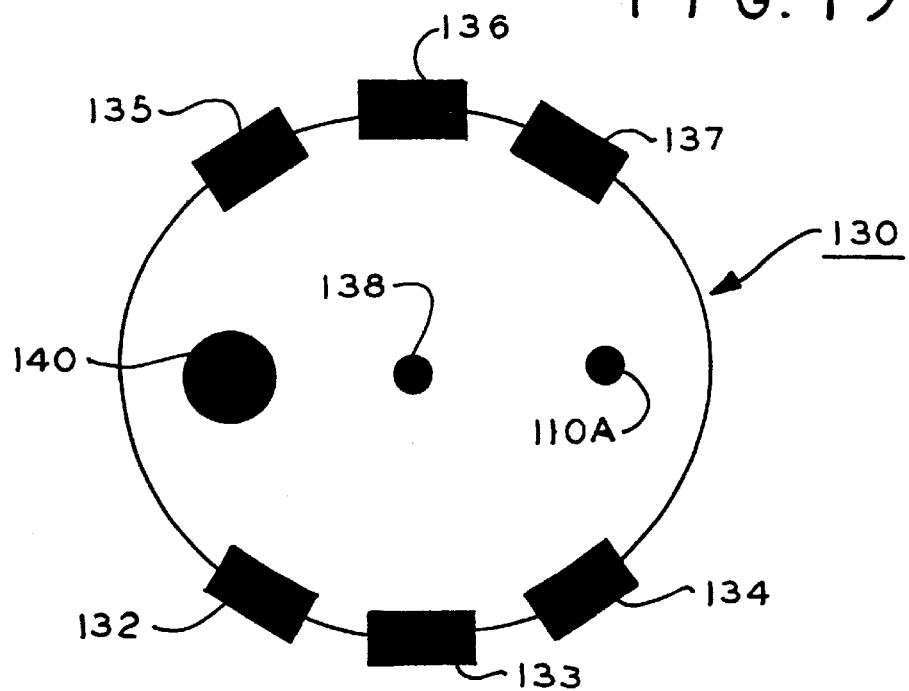

In FIG. 19, a detection array 130 is mounted on a support (not shown) in the measurement station. The support is positioned on a detection platform (not shown) at the measurement station. The detection array 130 includes a diffuse reflectance system comprising a diffuse reflectance light source 110A and detection zones 132–137, inclusive.

A profilometry system comprises profilometry light source lens 138. Lens 138 is part of a confocal system so that returned light passes through the same lens. The diffuse reflectance light source 110A is, for example, offset from the center point (where lens 138 is located) so that specular reflections, as opposed to diffuse reflections will be centered in an area 140 and away from the detector zones 132–137. These zones 132–137 include detectors that are preferably angled and arranged to accept only light from an appropriate direction.

After the dose (or diagnostic) unit measurement step, the robot 46 moves the electrostatic chuck 68 and the attached substrate 6 and frame assembly with the deposited powder/grains to the lamination station 54, FIG. 1a. During this period the reduced 400 V. holding signal is applied to the chuck electrodes at the collection zones CZ to hold the powder/grains to the chuck and the substrate flat against the chuck. The frame is continuously held to the chuck by the vacuum through the holes ECH, FIG. 11.

During deposition, a relatively high voltage, e.g., 2000 V as mentioned above, is used to create a deposition charge at each collection zone. This charge also holds the substrate flat against the electrostatic chuck during deposition. The charge also holds the dots of deposited powder/grains to the substrate which is in inverted orientation with the powder/grains beneath the substrate. After the desired deposition value has been sensed by the charge sensor circuit, the deposition voltage value is reduced sufficiently to stop the deposition of powder/grains. However, a charge is maintained at the reduced voltage sufficient to hold the base substrate 6 flat against the electrostatic chuck 68 and to hold the deposited powder/grains to the chuck as the chuck 68 is displaced to the measurement and lamination stations.

Just prior to this time, the substrate cover 4 is transported to the lamination station 54 by robot 56 from an input/output station 32. The cover 4 is placed on fixture 122. The depressions 8 of the cover 4 are placed in aligned mating depressions in the fixture 122. Alignment devices, e.g., pins and holes, on the frames of the substrate assemblies 32 and 34 and at the lamination station fixture 122 assure that the locations with the deposited powder/grains on the base substrate 4 are matched with the depressions 8 in the cover 4 substrate, FIG. 10.

The robot 46 then transports the base substrate 6 and frame assembly 34 from the measurement station 48 measuring apparatus 50 over the fixture 122 and places the substrate 6 with the deposited dosages on the cover substrate 4, FIG. 10. At this time the deposited dosages are no longer held in place by charges.

The robot 56 at the lamination station has vacuum cups (not shown) and an ultrasonic welding head 124. After the head of robot 46 moves away from the station 54, the robot 56 returns to perform the welding operation. The robot 56 head has a pad 126, FIG. 10, that holds the two substrates in intimate tight contact prior to the start of the welds. Once the other robot 46 releases the substrate 6, the electrostatic charge on the chuck 68 holding the deposited dosages in place is removed. The powder/grains are thus free to move about at this time. The pad 126 compresses the base substrate 6 against the cover substrate 4 to lock the powder/grains in place in the depressions 8 during the weld operation.

The weld head 124 then commences welding the substrates to form each unit form whether of dosage or diagnostic active ingredients. The welds may by made one form at a time or preferably by one or more weld heads simultaneously for all of the dosage forms on the substrates on the fixture 122. When the welds are complete, the robot 56 displaces to its idle position and the final package of dosage forms is removed for final processing into the package 2 (FIG. 1) or capsules 12 (FIG. 3a).

It will be appreciated that other sealing methods may be employed such as thermal or adhesive lamination. The illustrated bonding method is useful when one desires to keep the deposited powder/grains free of admixture with other components such as film polymers, though it will be recognized that this can be achieved in other ways.

In operation, covering frames and substrate assemblies 32 are stored at stations 30b and 30c, FIG. 1a. The frames are located by holes in the frames mating with pins in the stations. The base frames and substrate assemblies 34 are stored at station 30a and are also located by mating pins and holes. The robot 46, moves the receiver 64 to the station 30a. Alignment mechanisms in the receiver comprising alignment holes 65 and pins 67, FIGS. 13 and 14, mate with pins and holes at the input/output and alignment stations for aligning the robot receiver, and chuck 68 to the stored frame and substrate assemblies. Similar alignment mechanisms are located on the cover and welding robot 56.

In the profilometer process, robot 46 picks up the assembly 34 and carries it to the alignment station 44. Here the substrate assembly 34 is aligned to the electrostatic chuck via the alignment mechanisms 40, FIG. 13, on the chuck to assist in the alignment of the chuck to the substrate.

The assembly 34 is then transported from the alignment station 44 to the measurement station and aligned with the measurement apparatus 50. The apparatus 50 then scans the substrate 6 and records its distances at each of the collection zones CZ, FIG. 12, to the reference location as discussed above.

The robot 46 then transports the measured empty substrate 6 and frame assembly 34 to the deposition station 52. The frame is during this time secured to the chuck via the vacuum ports slot holes ECH. At the deposition station, the frame is placed on gasket 67 in a sealing relation therewith. Then the powder/grain deposition engine is turned on and the powder/grains deposited as described.

At the end of the deposition, the deposition voltage is reduced to stop the deposition, but maintained at the reduced value to hold the deposited powder/grains and substrate to the chuck. The robot 46 returns the substrate 6 and deposited powder/grains to the measuring station 48 to measure the distance to the deposited layers of powder/grains of active pharmaceutical ingredients or diagnostic ingredients at each zone CZ. The distances are measured and the volume amounts of deposited powder/grains calculated for each dosage or diagnostic collection zone. After measurement, if the calculated amount is outside the desired range from a predetermined amount, the information is displayed. The operator can then make adjustments to the voltages on the receiver to correct the deposition values.

In the alternative, automatic feed back can be provided to automatically adjust the voltages for a given set of collection zones. The system remembers which zones are defective and the operator or automated system can then remove and discard the out of specification unit dosage or diagnostic forms.

In an automated system, the laminated unit forms may be automatically transferred to a packaging station for screening out of specification unit forms and for packing the unit forms in the desired packaging.

It should be appreciated that there has been shown an apparatus and method for making a product containing a plurality of pharmaceutical or diagnostic unit dosage forms, each dosage form comprising at least one pharmaceutically or diagnostic active ingredient that does not vary from a predetermined amount by more than 5%.

It will occur to one of ordinary skill that various modifications may be made to the disclosed embodiments. Such modifications may include testing each unit dosage form by techniques other than laser scanning, for example.

Further, feedback may be provided based on the measured thickness of active ingredient for automatically adjustment such that the thickness of the deposited pharmaceutically or diagnostic active ingredient is reset during the measuring of the active ingredients of the next preceding formed plurality of unit dosage forms.

Further, while an induction device is preferred for inducing charges on the active ingredient particles, other known techniques may be used to charge these particles.

While a certain particle feed arrangement is disclosed for feeding the active ingredient particles, it will occur to one of ordinary skill that other feed arrangements may be provided as disclosed in the aforementioned patents in the introductory portion.

The present invention is also applicable to a package which includes separate units of diagnostic ingredients such as reagents for use in tests, antibodies, antigens and so on. The reagents may be part of a diagnostic kit unit which includes several different reagents.

With respect to a specific diagnostic reagent in a test, the test may include a plurality of separate units of the diagnostic reagent comprising the diagnostic reagent deposited on a substrate wherein the amount of diagnostic reagent in each unit does not vary from a predetermined amount by more than about 5%. Each unit of the diagnostic reagent may be In a separate package or vial in a kit or may be separate independent units in a single package or vial in a kit.

Cover Layer

As previously described, the cover layer is used in the electrostatic deposition process to cover the substrate thereby trapping the deposited active ingredient therebetween. Materials suitable for use as a cover layer advantageously possess the following properties: immediately soluble in all conditions of pH, temperature and the like; deformable to accept a range of doses; and easily dyed for color coding.

Candidate materials for a cover layer possessing the above-listed desirable properties include, without limitation, commerical hydroxypropylmethyl cellulose, methyl cellulose, hydroxypropyl cellulose, poly(vinyl pyrrolidinone), poly(vinyl alcohol), poly(ethylene oxide).

Sample Reservoir Layer

Where integrated diagnostic structural unit forms are desired instead of pharmaceutical dosage unit forms, a "spreading layer" or "sample reservoir layer" may be added in lieu of the above-described cover layer. The spreading layer is a porous layer, composed of particles of controlled particle size, which serves to retain and spread a sample of liquid which is to be assayed. For example, the spreading layer functions to trap cells or to retard the mobility of macromolecules such as proteins.

In general, the particles in the spreading layer should be inert and wettable. Additional properties of the spreading layer may include, for example, the ability to define a known volume of liquid in a known area, which is a function of particle size. In certain embodiments, the spreading layer provides a white or reflective surface for optical spectroscopy.

Preferred particulate materials for the spreading layer include commercially available latex beads with a diameter of from below 1 micron to several hundred microns, most preferably from about 40 to about 200 microns. Cellulose acetate or inorganic particulate materials such as barium sulfate also can be used. The distance between particles in the spreading layer should result in average pore sizes of from about 1.5 microns to about 50 microns, most preferably from about 10 to about 30 microns. The void volume in the spreading layer should range between from about 60% to about 90%.

Latex and cellulose acetate are preferred materials for the spreading layer because manufacturers can control the polymerization reaction for these materials and, thus, can control particle size. Control of particle size is important to control the volume of liquid retained, as previously discussed.

Moreover, with respect to electrostatic deposition of the spreading layer, particle size influences the degree of charging, deposition and, ultimately, the accuracy and uniformity of coverage. These relationships are well-known to those of skill in the art.

It is preferred that the particles of the spreading layer be deposited in a uniform layer with a thickness of at least a monolayer. The thickness of this layer will be dictated by particle size and by the desired volume capacity. Various geometries of the spreading layer, for example, a concave geometry to form a "cup" for the liquid sample, are also within the scope of the present invention.

Additional materials may be deposited onto, or codeposited with, the spreading layer. Such additional materials may include surfactants, carriers or binders (for example, polysaccharides), buffering agents, solvents or reagents for detection. Examples of reagents for detection that can be deposited electrostatically include, for example, those utilized in enzyme-coupled reactions, such as alkaline phosphatase.

Adhesives

Adhesives are used, in some embodiments, for bonding the substrate and cover layer together, and for bonding various overcoat/overwrap layers to other layers. For buccal, gingival and nasal locations, the adhesive advantageously provides good adhesion and is non-toxic. Suitable adhesives include, without limitation, synthetic rubber, acrylic pressure-sensitive adhesives, dental temporary, and maltodextrin. For dermal applications, the adhesive advantageously provides good adhesion and is non-allergenic. A suitable adhesive is the type used for adhesive bandages. For vaginal and rectal applications, the adhesive advantageously exhibits poor adhesion and is non-allergenic. A suitable adhesive is a "swell-in-place" material such as polysaccharide.

All patents and patent applications cited in this specification are incorporated herein by reference in their entirety. Any patent application to which this application claims priority is also incorporated herein by reference in its entirety.

It will be understood by those skilled in the art that variations in the illustrated devices and methods may suitably be used in conjunction with the present invention and that the invention may be practiced otherwise than as specifically described. Accordingly, this invention includes all modifications encompassed within the spirit and scope of the invention as defined by the claims that follow.

We claim:

1. A structural unit comprising an integrated diagnostic form, the diagnostic form comprising:
    a polymeric substrate;
    an active ingredient, electrostatically deposited on the surface of said substrate; and
    a porous spreading layer electrostatically deposited on the active ingredient, said spreading layer comprising particles of controlled particle size, wherein said spreading layer serves to retain and spread a sample of liquid which is to be diagnosed.

2. The structural unit of claim 1, wherein said active ingredient is present in an amount that does not vary from a target amount by more than about 5 weight percent.

3. The structural unit of claim 2, wherein said substrate comprises a planar film.

4. The structural unit of claim 3, wherein the particles of the spreading layer comprise latex beads with a diameter of from about 1 micron to about 200 microns.

5. The structural unit of claim 4, wherein the latex beads have a diameter of from about 40 microns to about 200 microns.

6. The structural unit of claim 3, wherein the particles of the spreading layer comprise cellulose acetate or inorganic particulate materials.

7. The structural unit of claim 3, wherein the distance between the particles in the spreading layer results in average pore sizes of from about 1.5 microns to about 50 microns.

8. The structural unit of claim 7, wherein the average pore size is from about 10 microns to about 30 microns.

9. The structural unit of claim 3, wherein the void volume in the spreading layer is between from about 60% to about 90%.

10. The structural unit of claim 3, wherein the particles of the spreading layer are deposited in a uniform layer with a thickness of at least a monolayer.

11. The structural unit of claim 3, further comprising an ingredient electrostatically deposited onto, or codeposited with, the spreading layer, such ingredient selected from the group consisting of surfactants, carriers, binders, buffering agents, solvents, and reagents for detection.

* * * * *